United States Patent [19]

Anthony et al.

[11] Patent Number: 5,258,360
[45] Date of Patent: Nov. 2, 1993

[54] ALPHAMETHOXY ACRYLIC ACID DERIVATIVES AS FUNGICIDES

[75] Inventors: Vivienne M. Anthony, Maidenhead; John M. Clough, Marlow; Paul deFraine, Wokingham; Christopher R. A. Godfrey, Bracknell; Kevin Beautement, Wokingham, all of England

[73] Assignee: Imperial Chemical Industries PLC, London, England

[21] Appl. No.: 915,594

[22] Filed: Jul. 21, 1992

Related U.S. Application Data

[62] Division of Ser. No. 734,791, Jul. 23, 1991, Pat. No. 5,160,364, which is a division of Ser. No. 378,076, Jul. 11, 1989, Pat. No. 5,053,073, which is a division of Ser. No. 39,449, Apr. 17, 1987, Pat. No. 4,863,503.

[30] Foreign Application Priority Data

Apr. 17, 1986 [GB] United Kingdom ............... 8609452

[51] Int. Cl.$^5$ ................... A01N 43/10; C07D 333/56
[52] U.S. Cl. ................... 504/289; 514/443; 549/49; 549/57; 549/58
[58] Field of Search ............... 549/58, 49, 57; 514/412, 443; 71/90, 95; 504/289

[56] References Cited

U.S. PATENT DOCUMENTS 4,826,531  5/1989  Anthony et al. ............. 514/269

FOREIGN PATENT DOCUMENTS 0079623  5/1983  European Pat. Off. .
433233   6/1991  European Pat. Off. .
2602372  7/1976  Fed. Rep. of Germany .
2709504  9/1977  Fed. Rep. of Germany .
2076801  9/1981  United Kingdom .

OTHER PUBLICATIONS

Nannini et al Chem Abst vol. 96 (1982) 96:68717b.
Schramm et al. Thesis, "Novel Antibiotics from Higher Fungi" (1980) with partial translation.

Primary Examiner—Mukund J. Shah
Assistant Examiner—Y. N. Gupta
Attorney, Agent, or Firm—Cushman, Darby & Cushman

[57] ABSTRACT

Compounds of formula (I):

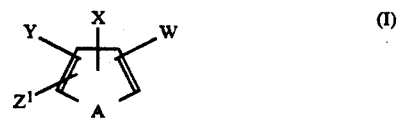

and stereoisomers thereof, wherein W is $R^1O_2C-C=CH-ZR^2$, wherein $R^1$ and $R^2$, which are the same or different, are alkyl or fluoroalkyl groups, and Z is either an oxygen or sulphur atom; A is an oxygen or sulphur atom, $-NR^3-$, or $-CR^4R^5-$; X, Y and $Z^1$, which are the same or different, are, for example, hydrogen, halogen, hydroxy, optionally substituted alkyl, cycloalkyl or aryl among other possible substituents or X and Y when they are in adjacent positions on the ring optionally form a fused ring; and R, $R^3$-$R^{12}$ are, for example, hydrogen or optionally substituted alkyl among other possible substituents provided $R^4$ and $R^5$ are not both hydrogen. The compounds are useful in agriculture, especially as fungicides but also as insecticides and plant growth regulators.

10 Claims, No Drawings

ALPHAMETHOXY ACRYLIC ACID DERIVATIVES AS FUNGICIDES

This is a division of Application Ser. No. 07/734,791, filed Jul. 23, 1991 now U.S. Pat. No. 5,160,364 which is a division of Ser. No. 07/378,076 filed Jul. 11, 1989 now U.S. Pat. No. 5,053,073 which is a division of Ser. No. 07/039,449, filed Apr. 17, 1987, now U.S. Pat. No. 4,863,503.

This invention relates to derivatives of acrylic acid useful in agriculture (especially as fungicides but also as insecticides and plant growth regulators), to processes for preparing them, to agricultural (especially fungicidal) compositions containing them, and to methods of using them to combat fungi, especially fungal infections in plants, to kill insect pests and to regulate plant growth.

The invention provides a compound having the general formula (I):

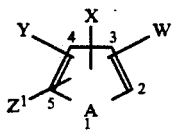

(I)

and stereoisomers thereof, wherein W is $R^1O_2C-C=CH-ZR^2$, wherein $R^1$ and $R^2$, which are the same or different, are alkyl or fluoroalkyl groups, and Z is either an oxygen or sulphur atom; A is an oxygen or sulphur atom, $-NR^3-$, or $-CR^4R^5-$; X, Y and $Z^1$, which are the same or different, are hydrogen or halogen atoms, or hydroxy, optionally substituted alkyl, optionally substituted cycloalkyl, optionally substituted cycloalkylalkyl, optionally substituted aralkyl, optionally substituted heteroarylalkyl, optionally substituted aryloxyalkyl, optionally substituted heteroaryloxyalkyl, optionally substituted alkenyl, optionally substituted alkynyl, optionally substituted aryl, optionally substituted heteroaryl, optionally substituted alkoxy, optionally substituted arylalkoxy, optionally substituted aryloxy, optionally substituted heteroaryloxy, optionally substituted acyloxy, optionally substituted amino, optionally substituted acylamino, optionally substituted arylazo, nitro, cyano, $-CO_2R^6$, $-CONR^7R^8$, $-COR^9$, $-CR=NR^{10}$, $-CR=NOR^{10}$, or $-N=CR^{11}R^{12}$ groups or the groups X and Y, when they are in adjacent positions on the ring, optionally join to form a fused ring, either aromatic or aliphatic, optionally containing one or more heteroatoms; and R, $R^3$, $R^4$, $R^5$, $R^6$, $R^7$, $R^8$, $R^9$, $R^{10}$, $R^{11}$ and $R^{12}$, which are the same or different, are hydrogen atoms (provided that $R^4$ and $R^5$ are not both hydrogen) or optionally substituted alkyl, optionally substituted cycloalkyl, optionally substituted cycloalkylalkyl, optionally substituted aralkyl, optionally substituted heteroarylalkyl, optionally substituted aryloxyalkyl, optionally substituted heteroaryloxyalkyl, optionally substituted alkenyl, optionally substituted alkynyl, optionally substituted aryl or optionally substituted heteroaryl groups; and metal complexes thereof.

The compounds of the invention contain at least one carbon-carbon double bond, and are sometimes obtained in the form of mixtures of geometric isomers. However, these mixtures can be separated into individual isomers, and this invention embraces such isomers, and mixtures thereof in all proportions, including those which consist substantially of the (Z)-isomer and those which consist substantially of the (E)-isomer.

The individual isomers which result from the unsymmetrically substituted double bond of the substituent W, are identified by the commonly used terms "E" and "Z". These terms are defined according to the Cahn-Ingold-Prelog system which is fully described in the literature (see, for example, J March, "Advanced Organic Chemistry", 3rd edition, Wiley-Interscience, page 109 et seq). Thus, for example, Compound No. 3 of Table I which follows:

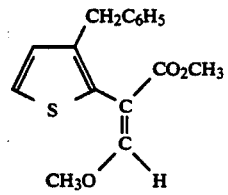

is the (z)-isomer, while Compound No. 36 of Table I which follows:

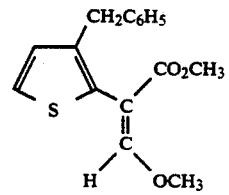

is the (E)-isomer. By contrast, Compound No. 3 of Table III (the furan analogue of the thiophene Compound No. 3 of Table I) which has the formula:

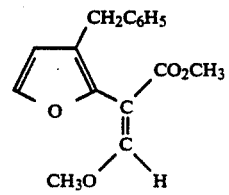

is the (E)-isomer.

Usually one isomer is more active fungicidally than the other, the more active isomer being the one in which the group $-ZR^2$ on the W substituent ($R^1O_2$-C—C=CH—$ZR^2$) is on the same side of the double bond as the 5-membered ring. This isomer is the (E)-isomer for all compounds of the invention except the thiophene compounds wherein the group W is at the 2-position of the ring, in which case this isomer is the (Z)-isomer. These isomers form a preferred embodiment of the invention.

In the compounds of formula (I), alkyl groups and the alkyl moiety of alkoxy groups can be in the form of straight or branched chains and preferably contain 1 to 6 carbon atoms, more preferably 1 to 4 carbon atoms. Examples are methyl, ethyl, propyl (n- and iso-propyl) and butyl (n-, sec-, iso- and tert-butyl). Optional substituents of alkyl include hydroxy, halogen (especially chlorine or fluorine), and alkoxycarbonyl. Trifluoromethyl is an optionally substituted alkyl group of particular interest.

$R^1$ and $R^2$, which are alkyl or fluoroalkyl groups, are preferably both methyl. Fluoroalkyl groups are preferably fluoromethyl containing one, two or three fluorine atoms.

Cycloalkyl, which is preferably $C_{3-6}$ cycloalkyl, includes cyclohexyl and cycloalkylalkyl, which is preferably $C_{3-6}$ cycloalkyl($C_{1-4}$)alkyl, includes cyclopropylethyl. Optional substituents include halogen (especially fluorine or chlorine), hydroxy and $C_{1-4}$ alkoxy.

Aralkyl includes, particularly, phenylalkyl (especially benzyl, phenylethyl, phenylpropyl, phenylbutyl or phenylhexyl) in which the alkyl moiety may carry other substituents such as hydroxy and the aryl moiety may be substituted with, for example, one or more of the following; halogen, hydroxy, $C_{1-4}$ alkyl (especially methyl and ethyl), $C_{1-4}$ alkoxy (especially methoxy), halo($C_{1-4}$) alkyl (especially trifluoromethyl), halo($C_{1-4}$)alkoxy (especially trifluoromethoxy), $C_{1-4}$ alkylthio (especially methylthio), $C_{1-4}$ alkoxy($C_{1-4}$)alkyl, $C_{3-6}$ cycloalkyl, $C_{3-6}$ cycloalkyl($C_{1-4}$)alkyl, aryl (especially phenyl), aryloxy (especially phenyloxy), aryl($C_{1-4}$)alkyl (especially benzyl, phenylethyl and phenyl n-propyl), aryl($C_{1-4}$)alkoxy (especially benzyloxy), aryloxy($C_{1-4}$)alkyl (especially phenyloxymethyl), acyloxy (especially acetyloxy and benzoyloxy), cyano, thiocyanato, nitro, —NR'R", —NHCOR', —NHCONR'R", —CONR'R", —COOR", —OSO$_2$R', —SO$_2$R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

Aryloxyalkyl includes, in particular, phenoxyalkyl (especially phenoxymethyl or phenoxyethyl) in which the alkyl moiety may carry other substituents such as hydroxy and the aryl moiety may be substituted in the same way as the aryl moiety in aralkyl above.

Heteroarylalkyl and heteroaryloxyalkyl mean alkyl (preferably $C_{1-4}$ alkyl and especially ethyl in the case of heteroarylalkyl and methyl in the case of heteroaryloxyalkyl) carrying a heteroaromatic substituent (linked by an oxygen atom in the case of heteroaryloxyalkyl) which includes pyridinyl, pyrimidinyl, thienyl, furyl and pyrrolyl. The heteroaromatic moiety is optionally substituted in the same way as the aryl moiety in aralkyl above, and particularly by trifluoromethyl, halogen (especially fluorine, chlorine or bromine), nitro, $C_{1-4}$ alkyl, $C_{1-4}$ alkoxy, trifluoromethoxy and amino.

Alkenyl and alkynyl groups preferably contain 2 to 6 carbon atoms and, more preferably, 2 to 4 carbon atoms in the form of straight or branched chains. Ethenyl, propenyl and butenyl are examples of alkenyl groups. Optional substituents of alkenyl (especially of ethenyl) include aromatic and heteroaromatic groups (such as phenyl, furyl, thienyl or pyridyl) which may themselves carry substituents such as those carried by the aryl moiety in aralkyl above, particularly halogen (especially chlorine or fluorine). Of particular interest are optionally substituted phenylethenyl and pyridinylethenyl. Further, the terminal carbon atom of the alkenyl groups may form part of a 5- or 6-membered cycloalkyl group. Alkynyl includes ethynyl and is optionally substituted by, for example, aryl which may itself be substituted in the same way as the aryl moiety in aralkyl above. Of particular interest is phenylethynyl.

Aryl is preferably phenyl; heteroaryl includes heteroaromatic groups such as pyridinyl, pyrimidinyl, pyrazinyl, pyridazinyl, 1,2,3-, 1,2,4-, and 1,3,5-triazinyl, 1,2,4-tetrazinyl, thienyl, quinolinyl, isoquinolinyl, quinoxalinyl and benzothiophenyl; either may be substituted in the same way as the aryl moiety in aralkyl above.

Alkoxy is preferably $C_{1-4}$ alkoxy and optionally substituted with, for example, hydroxy, halogen (especially chlorine or fluorine) and $C_{1-4}$ alkoxy. Arylalkoxy includes phenyl($C_{1-4}$)alkoxy (especially benzyloxy). Aryloxy includes phenyloxy and heteroaryloxy includes pyridinyl- and pyrimidinyl-oxy.

Acyloxy includes acetyloxy and benzoyloxy.

Optionally substituted amino and acylamino include the groups —NR'R" and —NHCOR' in which R' and R" defined above. Acylamino includes benzoylamino and furoylamino optionally substituted by, for example, N-($C_{1-4}$)alkyl (especially N-methyl).

The group —COR$^9$ includes, in particular, formyl, acetyl and optionally substituted benzoyl and the group —CR=NOR$^{10}$ includes the oxime ether —CH=N.OCH$_3$.

Arylazo is, for example, phenylazo in which the aryl moiety is optionally substituted in the same way as the aryl moiety in aralkyl above and particularly by alkynyl, alkoxy (especially methoxy) or dialkylamino (especially dimethylamino).

Whenever reference is made to an optionally substituted aryl or heteroaryl moiety, or optionally substituted fused ring, optional substituents include those which can be present in the aryl moiety of aralkyl as described above.

Compounds of formula (I) which are of particular interest, are those in which X, Y and Z are selected from the group consisting of hydrogen, halogen, $C_{1-4}$ alkyl, (especially methyl), aryl($C_{1-4}$)alkyl (especially benzyl, phenylethyl and phenyl n-propyl in which the phenyl ring is optionally substituted with, for example, halogen or nitro), acyl (especially formyl and benzoyl optionally substituted with, for example, halogen), heteroaryl($C_{1-4}$)alkyl, heteroaryloxy($C_{1-4}$)alkyl and heteroaryloxy in which the heteroaryl group is, for instance, pyridinyl, pyrimidinyl, pyridazinyl, pyrrolyl, furyl and particularly thienyl (examples are thienylethyl, thienyloxymethyl and pyridinyloxy), aryloxy($C_{1-4}$)alkyl (such as phenoxymethyl in which the phenyl ring is optionally substituted with, for example, halogen, methyl, methoxy or ethoxy), $C_{1-4}$ alkoxy (especially methoxy), aryl($C_{1-4}$)alkoxy (especially benzyloxy in which the phenyl ring is optionally substituted with, for example, halogen, methyl or methoxy), aryloxy (especially phenoxy) aryl($C_{2-4}$)alkenyl and heteroaryl($C_{2-4}$)alkenyl (especially phenylethenyl, pyridinylethenyl and thienyl-ethenyl which may be the (E)- or (Z)-isomers and in which the aromatic or heteroaromatic ring is optionally substituted with, for example, halogen, methyl or methoxy), aryl($C_{2-4}$)alkynyl (especially phenylethynyl), heteroaryl($C_{2-4}$)alkynyl, cyano, $C_{1-4}$ alkoxycarbonyl and aryloxycarbonyl (for example, n-propoxycarbonyl and phenyloxycarbonyl in which the phenyl ring is optionally substituted with, for instance, halogen). These compounds include those in which two of X, Y and $Z^1$ are hydrogen. It is preferred, though, that a group other than hydrogen is in a position on the heterocyclic ring adjacent to the substituent W. In the case when A is —NR$^3$—, this group may be R$^3$. When X and Y are in adjacent positions on the heterocyclic ring they may join to form a fused ring such as a fused benzene ring.

It is further preferred that at least one of $R^1$ and $R^2$ is methyl, more preferably $R^2$, and even more preferably, both.

It is still further preferred that A is sulphur or —$NR^3$—.

Yet a further preference is that Z (in the substituent W) is oxygen.

Thus in a particular embodiment of the invention, there is included the compound (IA)

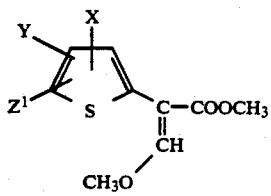

(IA)

preferably the (Z)-isomer when the acrylate group is in the 2-position, wherein X, which is in a position adjacent to the acrylate group, is halogen, $C_{1-4}$ alkyl, halo($C_{1-4}$)alkyl (especially halomethyl), aryl($C_{1-4}$)alkyl (especially benzyl, phenylethyl and phenyl n-propyl) aryloxy($C_{1-4}$)alkyl (especially phenyloxyalkyl), aryl-($C_{2-4}$)alkenyl (especially phenylethenyl), aryloxy (especially phenyloxy), acyl (especially formyl and benzoyl) and Y and $Z^1$ have any of the values previously defined for them but are preferably both hydrogen.

In another embodiment, there is included the compound (IB)

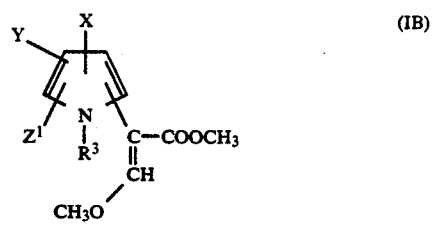

(IB)

wherein $R^3$ is hydrogen, $C_{1-4}$ alkyl (especially methyl or ethyl) or aryl($C_{1-4}$)alkyl (especially benzyl, phenylethyl and phenyl n-propyl); X is hydrogen, $C_{1-4}$ alkyl (especially methyl), aryl($C_{1-4}$)alkyl (especially benzyl, phenylethyl and phenyl n-propyl), aryl($C_{2-4}$)alkenyl (especially phenylethenyl), or acyl (especially formyl); and Y and $Z^1$ have any of the values previously defined for them, but are preferably both hydrogen; or when X is hydrogen Y and $Z^1$ together form a fused benzene ring.

Example of the compounds of the invention are shown in Tables I to VI.

TABLE I

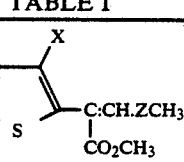

| COMPOUND NO. | Z | X | Y | $Z^1$ | ISOMER+ | OLEFINIC* | MELTING POINT (°C.) |
|---|---|---|---|---|---|---|---|
| 1 | O | H | H | H | Z | 7.55 | Oil |
| 2 | O | $CH_3$ | H | H | Z | 7.60 | Oil |
| 3 | O | $C_6H_5.CH_2$ | H | H | Z | 7.60 | Oil |
| 4 | O | $C_6H_5.CH_2CH_2$ | H | H | Z | 7.42 | Oil |
| 5 | O | $C_6H_5.CH_2CH_2$ | H | H | E | | |
| 6 | S | $C_6H_5.CH_2CH_2$ | H | H | Z | | |
| 7 | O | $C_6H_5.CH_2CH_2CH_2$ | H | H | Z | 7.48 | Oil |
| 8 | O | 2-$C_4H_3S.CH_2CH_2$≠ | H | H | Z | | |
| 9 | O | $C_6H_5.OCH_2$ | H | H | Z | 7.65 | Oil |
| 10 | O | $C_6H_5.OCH_2$ | H | H | E | 6.83 | Oil |
| 11 | S | $C_6H_5.OCH_2$ | H | H | Z | 8.04 | Oil |
| 12 | O | $C_6H_5.OCH_2$ | H | Cl | Z | | |
| 13 | O | $C_6H_5.OCH_2$ | H | H | Z | | |
| 14 | S | $C_6H_5.OCH_2$ | H | H | Z | | |
| 15 | O | $C_6H_5.OCH_2$ | $CH_3$ | H | Z | | |
| 16 | O | 2-$C_4H_3S.OCH_2$≠ | H | H | Z | | |
| 17 | O | (E)-$C_6H_5.CH:CH$ | H | H | Z | 7.71 | 133–134 |
| 18 | S | (E)-$C_6H_5.CH:CH$ | H | H | Z | | |
| 19 | O | (Z)-$C_6H_5.CH:CH$ | H | H | Z | | |
| 20 | O | $C_6H_5C:C$ | H | H | Z | | |
| 21 | O | (E)-2-$C_5H_4N.CH:CH$× | H | H | Z | | |
| 22 | O | 2-$C_5H_4N.O$× | H | H | Z | | |
| 23 | O | $C_6H_5.O$ | H | H | Z | 7.47 | Oil |
| 24 | O | $C_6H_5.CO$ | H | H | Z | | |
| 25 | S | $C_6H_5.CO$ | H | H | Z | | |
| 26 | O | $C_6H_5.CO$ | H | H | E | | |
| 27 | O | $C_6H_5.CO$ | CN | H | Z | | |
| 28 | O | 3-F—$C_6H_4.CO$ | H | H | Z | | |
| 29 | O | (E)-3-Cl—$C_6H_4.CH:CH$ | H | H | Z | | |
| 30 | O | 3-$CH_3O$—$C_6H_4.OCH_2$ | H | H | Z | | |
| 31 | O | $CH_3CH_2CH_2O_2C$ | H | H | Z | | |
| 32 | S | $CH_3CH_2CH_2O_2C$ | $CH_3$ | H | Z | | |
| 33 | O | $C_6H_5.O_2C$ | H | H | Z | | |
| 34 | O | 3-$NO_2.C_6H_4.CH_2CH_2$ | H | H | Z | | |
| 35 | O | 4-$CH_3.C_6H_4.CH_2O$ | H | H | Z | | |
| 36 | O | $C_6H_5.CH_2$ | H | H | E | 6.56 | Oil |
| 37 | S | $C_6H_5.OCH_2$ | H | H | E | 7.38 | Oil |

TABLE I-continued

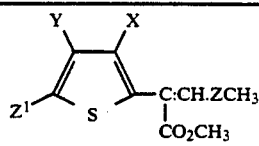

| COMPOUND NO. | Z | X | Y | Z¹ | ISOMER+ | OLEFINIC* | MELTING POINT (°C.) |
|---|---|---|---|---|---|---|---|
| 38 | O | 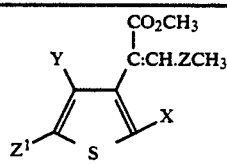 | H | H | Z | | |
| 39 | O | C₆H₅.O | H | H | E | 6.86 | Oil |

+Geometry of beta-methoxyacrylate or beta-(methylthio)acrylate group.
*Chemical shift of singlet from olefinic proton on beta-methoxyacrylate or beta-(methylthio)acrylate group (ppm from tetramethylsilane). Solvent:CDCl₃.
≠C₄H₃S is thienyl.
ˣC₅H₄N is pyridinyl.

TABLE II $$\underset{Z^1}{\overset{Y}{\diagdown}} \underset{S}{\diagdown} \overset{X}{\diagup} C(CO_2CH_3):CH.ZCH_3$$

| COMPOUND NO. | Z | X | Y | Z¹ | ISOMER+ | OLEFINIC* | MELTING POINT (°C.) |
|---|---|---|---|---|---|---|---|
| 1 | O | H | H | H | E | 7.50 | Oil |
| 2 | O | CH₃ | H | H | E | | |
| 3 | O | C₆H₅.CH₂ | H | H | E | 7.40 | Oil |
| 4 | O | C₆H₅.CH₂CH₂ | H | H | E | 7.54 | Oil |
| 5 | O | C₆H₅.CH₂CH₂ | H | H | Z | | |
| 6 | S | C₆H₅.CH₂CH₂ | H | H | E | | |
| 7 | O | C₆H₅.CH₂CH₂CH₂ | H | H | E | | |
| 8 | O | 2-C₄H₃S.CH₂CH₂≠ | H | H | E | | |
| 9 | O | C₆H₅.OCH₂ | H | H | E | 7.57 | Oil |
| 10 | O | C₆H₅.OCH₂ | H | H | Z | | |
| 11 | S | C₆H₅.OCH₂ | H | H | E | | |
| 12 | O | C₆H₅.OCH₂ | Br | H | E | | |
| 13 | O | C₆H₅.CH₂O | H | H | E | | |
| 14 | S | C₆H₅.CH₂O | H | H | E | | |
| 15 | O | C₆H₅.CH₂O | H | CH₃ | E | | |
| 16 | O | 2-C₄H₃S.OCH₂≠ | H | H | E | | |
| 17 | O | (E)-C₆H₅.CH:CH | H | H | E | 7.62 | 109–110 |
| 18 | S | (E)-C₆H₅.CH:CH | H | H | E | | |
| 19 | O | (Z)-C₆H₅.CH:CH | H | H | E | | |
| 20 | O | C₆H₅C:C | H | H | E | | |
| 21 | O | (E)-4-C₅H₄N.CH:CHˣ | H | H | E | | |
| 22 | O | 3-C₅H₄N.Oˣ | H | H | E | | |
| 23 | O | C₆H₅.O | H | H | E | | |
| 24 | O | C₆H₅.CO | H | H | E | 7.16 | 96–97 |
| 25 | S | C₆H₅.CO | H | H | E | | |
| 26 | O | C₆H₅.CO | H | H | Z | | |
| 27 | O | C₆H₅.CO | H | CN | E | | |
| 28 | O | 3-Cl—C₆H₄.CO | H | H | E | | |
| 29 | O | (E)-4-CH₃O—C₆H₄.CH:CH | H | H | E | | |
| 30 | O | 4-F—C₆H₄.OCH₂ | H | H | E | | |
| 31 | O | CH₃CH₂CH₂O₂C | H | H | E | | |
| 32 | S | CH₃CH₂CH₂O₂C | CH₃ | H | E | | |
| 33 | O | 3-Br—C₆H₅.O₂C | H | H | E | | |
| 34 | O | 4-NO₂—C₆H₄.CH₂CH₂ | H | H | E | | |
| 35 | O | 2-CH₃.C₆H₄.CH₂O | H | H | E | | |
| 36 | O | CH₃O.N:CHᵅ | H | H | E | See Table VII | 89–90 |
| 37 | O | CHO | H | H | E | 7.72 | 147–148 |
| 38 | O | CH₂Cl | H | H | E | 7.62 | 106–107 |
| 39 | O | Br | H | H | E | 7.58 | Oil |
| 40 | O | H | CH₃CH₂CH₂O₂C | H | E | 7.51 | Oil |
| 41 | O | H | C₆H₅.O₂C | H | E | | |
| 42 | O | H | C₆H₅.CO | H | E | | |

TABLE II-continued $$\underset{Z^1}{\overset{Y}{\diagdown}}\underset{S}{\overset{}{\diagdown}}\overset{\overset{CO_2CH_3}{|}}{\underset{X}{\overset{C:CH.ZCH_3}{\diagup}}}$$

| COMPOUND NO. | Z | X | Y | $Z^1$ | ISOMER[+] | OLEFINIC[*] | MELTING POINT (°C.) |
|---|---|---|---|---|---|---|---|
| 43 | O | H | $C_6H_5.CH_2CH_2$ | H | E | | |
| 44 | O | H | (E)-$C_6H_5$:CH:CH | H | E | | |
| 45 | O | H | $C_6H_5.OCH_2$ | H | E | | |
| 46 | O | H | $C_6H_5.CH_2O$ | H | E | | |
| 47 | O | H | $C_6H_5O$ | H | E | | |
| 48 | S | H | 3-$CH_3O$—$C_6H_4.OCH_2$ | H | E | | |
| 49 | S | H | (E)-3-$C_4H_3S.CH:CH$[*] | H | E | | |
| 50 | S | H | $C_6H_5.CH_2O$ | H | E | | |
| 51 | O | H | $C_6H_5.OCH_2$ | H | Z | | |
| 52 | O | H | 3,5-di-F—$C_6H_3.CO$ | H | Z | | |
| 53 | O | F | $C_6H_5.OCH_2$ | H | E | | |
| 54 | O | H | 4-$NO_2$—$C_6H_4.CH_2CH_2$ | $CH_3$ | E | | |
| 55 | O | Cl | $CH_3CH_2O_2C$ | Cl | E | | |
| 56 | O | H | | | E | | |
| 57 | O | H | | | E | | |
| 58 | O | 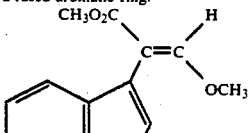 | H | H | E | | |

Substituents link to form a fused aromatic ring.

Thus Compound No. 56 is: 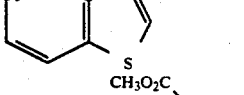

Thus Compound No. 57 is: 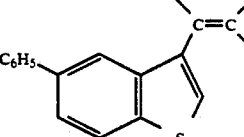

[+] Geometry of beta-methoxyacrylate or beta-(methylthio)acrylate group.
[*] Chemical shift of singlet from olefinic proton on beta-methoxyacrylate or beta-(methylthio)acrylate group (ppm from tetramethylsilane). Solvent:$CDCl_3$.
[+] $C_4H_3S$ is thienyl.
[x] $C_5H_4N$ is pyridinyl.
[a] Single isomer, geometry not assigned.

TABLE III $$\underset{Z^1}{\overset{Y}{\diagdown}}\underset{O}{\overset{X}{\diagdown}}\overset{\overset{C:CH.ZCH_3}{|}}{\underset{CO_2CH_3}{\diagup}}$$

| COMPOUND NO. | Z | X | Y | $Z^1$ | ISOMER[+] | OLEFINIC[*] | MELTING POINT (°C.) |
|---|---|---|---|---|---|---|---|
| 1 | O | H | H | H | E | 7.45 | Oil |
| 2 | O | $CH_3$ | H | H | E | | |
| 3 | O | $C_6H_5.CH_2$ | H | H | E | | |
| 4 | O | $C_6H_5.CH_2CH_2$ | H | H | E | 7.57 | Oil |
| 5 | O | $C_6H_5.CH_2CH_2$ | H | H | Z | | |
| 6 | S | $C_6H_5.CH_2CH_2$ | H | H | E | | |
| 7 | O | $C_6H_5.CH_2CH_2CH_2$ | H | H | E | | |
| 8 | O | 2-$C_4H_3S.CH_2CH_2$[≠] | H | H | E | | |
| 9 | O | $C_6H_5.OCH_2$ | H | H | E | | |
| 10 | O | $C_6H_5.OCH_2$ | H | H | Z | | |
| 11 | S | $C_6H_5.OCH_2$ | H | H | E | | |
| 12 | O | $C_6H_5.OCH_2$ | H | Cl | E | | |
| 13 | O | $C_6H_5.CH_2O$ | H | H | E | | |

TABLE III-continued

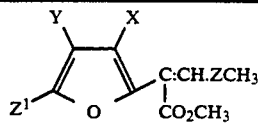

| COMPOUND NO. | Z | X | Y | Z¹ | ISOMER+ | OLEFINIC* | MELTING POINT (°C.) |
|---|---|---|---|---|---|---|---|
| 14 | S | $C_6H_5.CH_2O$ | H | H | E | | |
| 15 | O | $C_6H_5.CH_2O$ | $CH_3$ | H | E | | |
| 16 | O | $2\text{-}C_4H_3S.OCH_2 \neq$ | H | H | E | | |
| 17 | O | $(E)\text{-}C_6H_5.CH:CH$ | H | H | E | 7.70 | 107 |
| 18 | S | $(E)\text{-}C_6H_5.CH:CH$ | H | H | E | | |
| 19 | O | $(Z)\text{-}C_6H_5.CH:CH$ | H | H | E | | |
| 20 | O | $C_6H_5C:C$ | H | H | E | | |
| 21 | O | $(E)\text{-}2\text{-}C_5H_4N.CH:CH^x$ | H | H | E | | |
| 22 | O | $2\text{-}C_5H_4N.O^x$ | H | H | E | | |
| 23 | O | $C_6H_5.O$ | H | H | E | | |
| 24 | O | $C_6H_5.CO$ | H | H | E | | |
| 25 | S | $C_6H_5.CO$ | H | H | E | | |
| 26 | O | $C_6H_5.CO$ | H | H | Z | | |
| 27 | O | $C_6H_5.CO$ | CN | H | E | | |
| 28 | O | $3\text{-}F\text{—}C_6H_4.CO$ | H | H | E | | |
| 29 | O | $(E)\text{-}3\text{-}Cl\text{—}C_6H_4.CH:CH$ | H | H | E | | |
| 30 | O | $3\text{-}CH_3O\text{—}C_6H_4.OCH_2$ | H | H | E | | |
| 31 | O | $CH_3CH_2CH_2O_2C$ | H | H | E | | |
| 32 | S | $CH_3CH_2CH_2O_2C$ | $CH_3$ | H | E | | |
| 33 | O | $C_6H_5.O_2C$ | H | H | E | | |
| 34 | O | $3\text{-}NO_2.C_6H_4.CH_2CH_2$ | H | H | E | | |
| 35 | O | $3\text{-}CH_3.C_6H_4.CH_2O$ | H | H | E | | |
| 36 | O | $C_6H_5.CH_2$ | H | H | Z | | |
| 37 | S | $C_6H_5.OCH_2$ | H | H | Z | | |

+Geometry of beta-methoxyacrylate or beta-(methylthio)acrylate group.
*Chemical shift of singlet from olefinic proton on beta-methoxyacrylate or beta-(methylthio)acrylate group (ppm from tetramethylsilane). Solvent:CDCl₃.
≠$C_4H_3S$ is thienyl.
x$C_5H_4N$ is pyridinyl.

TABLE IV

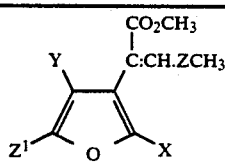

| COMPOUND NO. | Z | X | Y | Z¹ | ISOMER+ | OLEFINIC* | MELTING POINT (°C.) |
|---|---|---|---|---|---|---|---|
| 1 | O | H | H | H | E | 7.48 | Oil |
| 2 | O | $CH_3$ | H | H | E | | |
| 3 | O | $C_6H_5.CH_2$ | H | H | E | 7.50 | Oil |
| 4 | O | $C_6H_5.CH_2CH_2$ | H | H | E | | |
| 5 | O | $C_6H_5.CH_2CH_2$ | H | H | Z | | |
| 6 | S | $C_6H_5.CH_2CH_2$ | H | H | E | | |
| 7 | O | $C_6H_5.CH_2CH_2CH_2$ | H | H | E | | |
| 8 | O | $2\text{-}C_4H_3S.CH_2CH_2 \neq$ | H | H | E | | |
| 9 | O | $C_6H_5.OCH_2$ | H | H | E | | |
| 10 | O | $C_6H_5.OCH_2$ | H | H | Z | | |
| 11 | S | $C_6H_5.OCH_2$ | H | H | E | | |
| 12 | O | $C_6H_5.OCH_2$ | Br | H | E | | |
| 13 | O | $C_6H_5.CH_2O$ | H | H | E | | |
| 14 | S | $C_6H_5.CH_2O$ | H | H | E | | |
| 15 | O | $C_6H_5.CH_2O$ | H | $CH_3$ | E | | |
| 16 | O | $2\text{-}C_4H_3S.OCH_2 \neq$ | H | H | E | | |
| 17 | O | $(E)\text{-}C_6H_5.CH:CH$ | H | H | E | | |
| 18 | S | $(E)\text{-}C_6H_5.CH:CH$ | H | H | E | | |
| 19 | O | $(Z)\text{-}C_6H_5.CH:CH$ | H | H | E | | |
| 20 | O | $C_6H_5.C:C$ | H | H | E | | |
| 21 | O | $(E)\text{-}4\text{-}C_5H_4N.CH:CH^x$ | H | H | E | | |
| 22 | O | $3\text{-}C_5H_4N.O^x$ | H | H | E | | |
| 23 | O | $C_6H_5.O$ | H | H | E | | |
| 24 | O | $C_6H_5.CO$ | H | H | E | | |
| 25 | S | $C_6H_5.CO$ | H | H | E | | |
| 26 | O | $C_6H_5.CO$ | H | H | Z | | |
| 27 | O | $C_6H_5.CO$ | H | CN | E | | |
| 28 | O | $3\text{-}Cl\text{—}C_6H_4.CO$ | H | H | E | | |

TABLE IV-continued

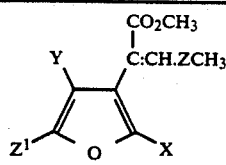

| COMPOUND NO. | Z | X | Y | Z¹ | ISOMER+ | OLEFINIC* | MELTING POINT (°C.) |
|---|---|---|---|---|---|---|---|
| 29 | O | (E)-4-CH$_3$O—C$_6$H$_4$.CH:CH | H | H | E | | |
| 30 | O | 4-F—C$_6$H$_4$.OCH$_2$ | H | H | E | | |
| 31 | O | CH$_3$CH$_2$CH$_2$O$_2$C | H | H | E | | |
| 32 | S | CH$_3$CH$_2$CH$_2$O$_2$C | CH$_3$ | H | E | | |
| 33 | O | 3-Br—C$_6$H$_5$.O$_2$C | H | H | E | | |
| 34 | O | 4-NO$_2$—C$_6$H$_4$.CH$_2$CH$_2$ | H | H | E | | |
| 35 | O | 2-CH$_3$.C$_6$H$_4$.CH$_2$O | H | H | E | | |
| 36 | O | CH$_3$O.N:CH$^a$ | H | H | E | | |
| 37 | O | CHO | H | H | E | 7.68 | 124 |
| 38 | O | CH$_2$Cl | H | H | E | | |
| 39 | O | Br | H | H | E | | |
| 40 | O | H | CH$_3$CH$_2$CH$_2$O$_2$C | H | E | | |
| 41 | O | H | C$_6$H$_5$.O$_2$C | H | E | | |
| 42 | O | H | C$_6$H$_5$.CO | H | E | | |
| 43 | O | H | C$_6$H$_5$.CH$_2$CH$_2$ | H | E | | |
| 44 | O | H | (E)-C$_6$H$_5$.CH:CH | H | E | | |
| 45 | O | H | C$_6$H$_5$.OCH$_2$ | H | E | | |
| 46 | O | H | C$_6$H$_5$.CH$_2$O | H | E | | |
| 47 | O | H | C$_6$H$_5$O | H | E | | |
| 48 | S | H | 3-CH$_3$O—C$_6$H$_4$.OCH$_2$ | H | E | | |
| 49 | S | H | (E)-3-C$_4$H$_3$S.CH:CH$^{\neq}$ | H | E | | |
| 50 | S | H | C$_6$H$_5$.CH$_2$O | H | E | | |
| 51 | O | H | C$_6$H$_5$.OCH$_2$ | H | Z | | |
| 52 | O | H | 3,5-di-F—C$_6$H$_3$.CO | H | Z | | |
| 53 | O | F | C$_6$H$_5$.OCH$_2$ | H | E | | |
| 54 | O | H | 4-NO$_2$—C$_6$H$_4$.CH$_2$CH$_2$ | CH$_3$ | E | | |
| 55 | O | Cl | CH$_3$CH$_2$O$_2$C | Cl | E | | |
| 56 | O | H | | | E | | |
| 57 | O | H | | | E | | |
| 58 | O | CH$_3$ | | | E | 7.67 | 67–68 |

$^a$ Substituents link to form a fused aromatic ring.

Thus Compound No. 56 is: 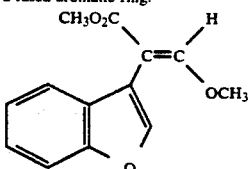

Compound No. 57 is: 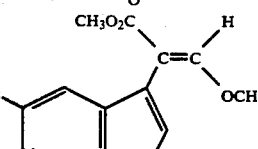

Compound No. 58 is: 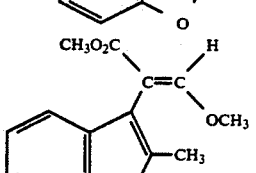

+Geometry of beta-methoxyacrylate or beta-(methylthio)acrylate group.
*Chemical shift of singlet from olefinic proton on beta-methoxyacrylate or beta-(methylthio)acrylate group (ppm from tetramethylsilane). Solvent:CDCl$_3$.
$^{\neq}$C$_4$H$_3$S is thienyl.
$^x$C$_5$H$_4$N is pyridinyl.

TABLE V

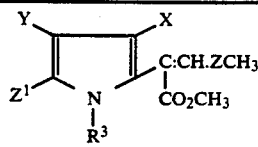

| COMPOUND NO. | Z | X | R$^3$ | Y | Z$^1$ | ISOMER+ | OLEFINIC* | MELTING POINT (°C.) |
|---|---|---|---|---|---|---|---|---|
| 1 | O | H | CH$_3$CH$_2$ | H | H | E | | |
| 2 | O | CH$_3$ | CH$_3$ | H | H | E | | |
| 3 | O | C$_6$H$_5$.CH$_2$ | CH$_3$ | H | H | E | | |
| 4 | O | C$_6$H$_5$.CH$_2$CH$_2$ | CH$_3$ | H | H | E | | |
| 5 | O | C$_6$H$_5$.CH$_2$CH$_2$CH$_2$ | CH$_3$ | H | H | E | | |
| 6 | O | 2-C$_4$H$_3$S.CH$_2$CH$_2$≠ | CH$_3$ | H | H | E | | |
| 7 | O | C$_6$H$_5$.OCH$_2$ | CH$_3$ | H | H | E | | |
| 8 | O | C$_6$H$_5$.CO | CH$_3$ | H | H | E | | |
| 9 | O | 3-C$_4$H$_3$S.OCH$_2$≠ | CH$_3$ | H | H | E | | |
| 10 | O | (E)-C$_6$H$_5$.CH:CH | CH$_3$ | H | H | E | | |
| 11 | S | (Z)-C$_6$H$_5$.CH:CH | CH$_3$ | H | H | E | | |
| 12 | O | C$_6$H$_5$.C:C | CH$_3$ | H | H | E | | |
| 13 | O | (E)-2-C$_5$H$_4$N.CH:CH$^x$ | CH$_3$ | H | H | E | | |
| 14 | O | 2-C$_5$H$_4$N.CH$_2$CH$_2$$^x$ | CH$_3$ | H | H | E | | |
| 15 | O | 3,4-di-Cl—C$_6$H$_3$.CO | CH$_3$ | H | H | E | | |
| 16 | O | CH$_3$.CO | CH$_3$ | H | H | E | | |
| 17 | O | 3-CH$_3$—C$_6$H$_4$.OCH$_2$ | CH$_3$ | H | H | E | | |
| 18 | O | CH$_3$CH$_2$CH$_2$O$_2$C | CH$_3$ | H | H | E | | |
| 19 | O | C$_6$H$_5$.O$_2$C | CH$_3$ | H | H | E | | |
| 20 | O | 4-F—C$_6$H$_4$.OCH$_2$ | CH$_3$ | H | H | E | | |
| 21 | S | C$_6$H$_5$.OCH$_2$ | CH$_3$ | H | H | E | | |
| 22 | S | (E)-C$_6$H$_5$.CH:CH | CH$_3$ | H | H | E | | |
| 23 | S | C$_6$H$_5$.C:C | CH$_3$ | H | H | E | | |
| 24 | O | C$_6$H$_5$.CO | H | H | H | E | | |
| 25 | O | 3-F—C$_6$H$_4$.CH$_2$CH$_2$ | CH$_3$CH$_2$ | H | H | E | | |
| 26 | O | 3-C$_5$H$_4$N.OCH$_2$$^x$ | C$_6$H$_5$ | H | H | E | | |
| 27 | O | 3-CH$_3$—C$_6$H$_4$.CO | CH$_3$ | Br | H | E | | |
| 28 | O | (E)-2-C$_4$H$_3$S.CH$_2$CH$_2$≠ | CH$_3$ | CH$_3$ | H | E | | |
| 29 | O | CH$_3$CH$_2$CH$_2$O$_2$C | CH$_3$ | H | Cl | E | | |
| 30 | O | C$_6$H$_5$.CH$_2$CH$_2$ | CH$_3$ | H | CH$_3$ | E | | |
| 31 | O | C$_6$H$_5$.CH$_2$CH$_2$ | CH$_3$ | H | H | Z | | |
| 32 | O | C$_6$H$_5$.OCH$_2$ | CH$_3$ | H | H | Z | | |
| 33 | O | C$_6$H$_5$.CO | CH$_3$ | H | H | Z | | |
| 34 | O | H | C$_6$H$_5$.CH$_2$CH$_2$ | H | H | E | 7.66 | 72–73 |
| 35 | O | H | (E)-C$_6$H$_5$.CH:CH | H | H | E | | |
| 36 | O | H | C$_6$H$_5$.OCH$_2$ | H | H | E | | |
| 37 | O | H | C$_6$H$_5$.CO | H | H | E | | |
| 38 | O | H | CH$_3$ | H | H | E | 7.62 | 58 |
| 39 | O | H | C$_6$H$_5$.CH$_2$ | H | H | E | | |
| 40 | O | H | CH$_3$CH$_2$CH$_2$O$_2$C | H | H | E | | |
| 41 | O | H | 2-C$_4$H$_3$S.CH$_2$CH$_2$≠ | H | H | E | | |
| 42 | O | H | 2-C$_5$H$_4$N.OCH$_2$$^x$ | H | H | E | | |
| 43 | O | H | 3-CH$_3$O—C$_6$H$_5$.CH$_2$CH$_2$ | H | H | E | | |
| 44 | O | H | 2,5-di-Cl—C$_6$H$_5$.CO | H | H | E | | |
| 45 | O | H | 4-CH$_3$CH$_2$O—C$_6$H$_4$.OCH$_2$ | H | H | E | | |
| 46 | S | H | C$_6$H$_5$.CH$_2$CH$_2$ | H | H | E | | |
| 47 | S | H | (E)-C$_6$H$_5$.CH:CH | H | H | E | | |
| 48 | S | H | C$_6$H$_5$.OCH$_2$ | H | H | E | | |
| 49 | O | Cl | C$_6$H$_5$.CO | H | H | E | | |
| 50 | O | CH$_3$ | 3-CH$_3$CH$_2$O—C$_6$H$_4$.OCH$_2$ | H | H | E | | |
| 51 | O | H | C$_6$H$_5$.CH$_2$ | CH$_3$CH$_2$ | H | E | | |
| 52 | O | H | CH$_3$CH$_2$CH$_2$O$_2$C | Br | H | E | | |
| 53 | O | H | 2-C$_4$H$_3$S.CH$_2$CH$_2$≠ | H | Cl | E | | |
| 54 | O | H | 4-C$_5$H$_4$N.OCH$_2$$^x$ | H | CH$_3$ | E | | |
| 55 | O | H | 3-CH$_4$O—C$_6$H$_4$.CH$_2$CH$_2$ | H | H | Z | | |
| 56 | O | H | 3,4-di-CH$_3$—C$_6$H$_3$.CO | H | H | Z | | |
| 57 | O | H | C$_6$H$_5$.CH$_2$ | H | CH$_3$ | E | 7.52 | 102–103 |
| 58 | O | H | CH$_3$-N-N=...-CH$_3$ / -OCH$_2$ (pyridazinone) | H | H | E | | |
| 59 | O | CHO | CH$_3$ | H | H | E | | |
| 60 | O | CH$_2$OH | CH$_3$ | H | H | E | | |
| 61 | O | H | H | H | H | E | 7.40 | Oil |
| 62 | O | H | C$_6$H$_5$.CH(OCOCH$_3$)CH$_2$ | H | H | E | 7.66 | Oil |

TABLE V-continued

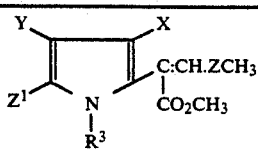

| COMPOUND NO. | Z | X | R³ | Y | Z¹ | ISOMER+ | OLEFINIC* | MELTING POINT (°C.) |
|---|---|---|---|---|---|---|---|---|
| 63 | O | H | C₆H₅.CH(OCOCH₃)CH₂ | H | H | Z | 6.23 | Oil |

+Geometry of beta-methoxyacrylate or beta-(methylthio)acrylate group.
*Chemical shift of singlet from olefinic proton on beta-methoxyacrylate or beta-(methylthio)acrylate group (ppm from tetramethylsilane). Solvent:CDCl₃.
≠C₄H₃S is thienyl.
ˣC₅H₄N is pyridinyl.

TABLE VI

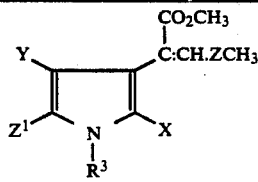

| COMPOUND NO. | Z | X | Y | R³ | Z¹ | ISOMER+ | OLEFINIC* | MELTING POINT (°C.) |
|---|---|---|---|---|---|---|---|---|
| 1 | O | H | H | CH₃ | H | E | 7.36 | Oil |
| 2 | O | CH₃ | H | CH₃ | H | E | | |
| 3 | O | C₆H₅.CH₂ | H | CH₃ | H | E | | |
| 4 | O | C₆H₅.CH₂CH₂ | H | CH₃ | H | E | 7.51 | Oil |
| 5 | O | C₆H₅.CH₂CH₂CH₂ | H | CH₃ | H | E | | |
| 6 | O | 2-C₄H₃S.CH₂CH₂≠ | H | CH₃ | H | E | | |
| 7 | O | C₆H₅.OCH₂ | H | CH₃ | H | E | | |
| 8 | O | C₆H₅.CO | H | CH₃ | H | E | | |
| 9 | O | 3-C₄H₃S.OCH₂≠ | H | CH₃ | H | E | | |
| 10 | O | (E)-C₆H₅.CH:CH | H | CH₃ | H | E | 7.50 | Oil |
| 11 | S | (Z)-C₆H₅.CH:CH | H | CH₃ | H | E | 7.29 | Oil |
| 12 | O | C₆H₅.C:C | H | CH₃ | H | E | | |
| 13 | O | (E)-2-C₅H₄N.CH:CHˣ | H | CH₃ | H | E | | |
| 14 | O | 2-C₅H₄N.CH₂CH₂ˣ | H | CH₃ | H | E | | |
| 15 | O | 3,4-di-F—C₆H₃.CO | H | CH₃ | H | E | | |
| 16 | O | CH₃CO | H | CH₃ | H | E | | |
| 17 | O | 3-CH₃O—C₆H₄.OCH₂ | H | CH₃ | H | E | | |
| 18 | O | CH₃CH₂CH₂O₂C | H | CH₃ | H | E | | |
| 19 | O | C₆H₅.O₂C | H | CH₃ | H | E | | |
| 20 | O | 4-F—C₆H₄.OCH₂ | H | CH₃ | H | E | | |
| 21 | S | C₆H₅.OCH₂ | H | CH₃ | H | E | | |
| 22 | S | (E)-C₆H₅.CH:CH | H | CH₃ | H | E | | |
| 23 | S | C₆H₅.C:C | H | CH₃ | H | E | | |
| 24 | O | C₆H₅.CO | H | H | H | E | | |
| 25 | O | 3-F—C₆H₄.CH₂CH₂ | H | CH₃CH₂ | H | E | | |
| 26 | O | 3-C₅H₄N.OCH₂ˣ | H | C₆H₅ | H | E | | |
| 27 | O | 3-CH₃O—C₆H₄.CO | Br | CH₃ | H | E | | |
| 28 | O | (E)-3-C₄H₃S.CH:CH≠ | CH₃ | CH₃ | H | E | | |
| 29 | O | CH₃CH₂CH₂O₂C | H | CH₃ | CH₃ | E | | |
| 30 | O | C₆H₅.CH₂CH₂ | H | CH₃ | Cl | E | | |
| 31 | O | C₆H₅.CH₂CH₂ | H | CH₃ | H | Z | | |
| 32 | O | C₆H₅.OCH₂ | H | CH₃ | H | Z | | |
| 33 | O | C₆H₅.CO | H | CH₃ | H | Z | | |
| 34 | O | H | (E)-C₆H₅.CH:CH | CH₃ | H | E | | |
| 35 | O | H | C₆H₅.OCH₂ | CH₃ | H | E | | |
| 36 | O | H | C₆H₅.CO | CH₃ | H | E | | |
| 37 | O | H | CH₃ | CH₃ | H | E | | |
| 38 | O | H | C₆H₅.CH₂ | CH₃ | H | E | | |
| 39 | O | H | CH₃CH₂CH₂O₂C | CH₃ | H | E | | |
| 40 | O | H | 2-C₄H₃S.CH₂CH₂+ | CH₃ | H | E | | |
| 41 | O | H | 2-C₅H₄N.OCH₂ˣ | CH₃ | H | E | | |
| 42 | O | H | 3-Cl—C₆H₄.CH₂CH₂ | CH₃ | H | E | | |
| 43 | O | H | 3-Cl—C₆H₄.CO | CH₃ | H | E | | |
| 44 | O | H | C₆H₅.CH₂CH₂ | CH₃ | H | E | | |
| 45 | O | H | 3-CH₃CH₂O—C₆H₄.OCH₂ | CH₃ | H | E | | |
| 46 | S | H | C₆H₅.CH₂CH₂ | H | H | E | | |
| 47 | S | H | (E)-C₆H₅.CH:CH | H | H | E | | |
| 48 | S | H | C₆H₅.OCH₂ | H | H | E | | |
| 49 | O | Cl | C₆H₅.CO | H | H | E | | |
| 50 | O | CH₃ | 3-CH₃—C₆H₄.OCH₂ | H | H | E | | |

TABLE VI-continued

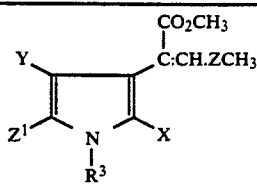

| COMPOUND NO. | Z | X | Y | R³ | Z¹ | ISOMER+ | OLEFINIC* | MELTING POINT (°C.) |
|---|---|---|---|---|---|---|---|---|
| 51 | O | H | C₆H₅.CH₂ | CH₃CH₂ | H | E | | |
| 52 | O | H | CH₃CH₂O₂C | C₆H₅ | H | E | | |
| 53 | O | H | 3-C₄H₃S.CH₂CH₂≠ | H | Br | E | | |
| 54 | O | H | 2-C₅H₄N.OCH₂ˣ | H | CH₃ | E | | |
| 55 | O | H | 4-CH₃O—C₆H₄.CH₂CH₂ | H | H | Z | | |
| 56 | O | H | 3,5-di-CH₃—C₆H₃.CO | H | H | Z | | |
| 57 | O | H | ○ | H | ○ | E | 7.60 | 110–112 |
| 58 | O | H | ○ | CH₃ | ○ | E | 7.56 | Oil |
| 59 | O | H | H | H | H | E | 7.31 | Oil |
| 60 | O | CHO | H | CH₃ | H | E | 7.65 | 82–84 |
| 61 | O | HO.CH₂ | H | CH₃ | H | E | | |
| 62 | O | H | H | CH₃ | CHO | E | 7.47 | Oil |

+Geometry of beta-methoxyacrylate or beta-(methylthio)acrylate group.
*Chemical shift of singlet from olefinic proton on beta-methoxyacrylate or beta-(methylthio)acrylate group (ppm from tetramethylsilane). Solvent:CDCl₃.
≠C₄H₃S is thienyl.
ˣC₅H₄N is pyridinyl.
○Substituents link to form a fused benzene ring.

Compound 57 is: 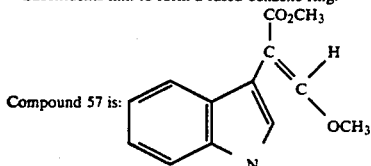

Compound 58 is: 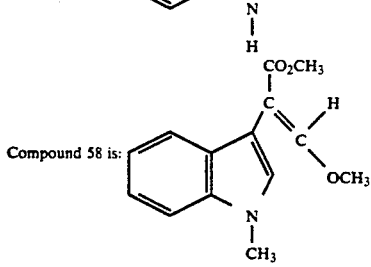

TABLE VII

TABLE VII: SELECTED PROTON NMR DATA
Table VII shows selected proton nmr data for certain compounds described in Tables I to VI. Chemical shifts are measured in ppm from tetramethylsilane, and deuterochloroform was used as solvent throughout.
The following abbreviations are used:

| br = broad | t = triplet |
| s = singlet | q = quartet |
| d = doublet | m = multiplet |

| TABLE NO. | COMPOUND NO. | |
|---|---|---|
| I | 1 | 3.80(3H, s), 3.97(3H, s), 7.00–7.55(3H, m), 7.55(1H, s)ppm. |
| I | 3 | 3.64(3H, s), 3.78(6H, s), 6.75 (1H, d), 7.00–7.40(6H, m), 7.60 (1H, s)ppm. |
| I | 4 | 2.40–2.90(4H, m), 3.60(3H, s), 3.75(3H, s), 6.70(1H, d), 6.80–7.20(6H, m), 7.42(1H, s)ppm. |
| I | 7 | 1.60–2.00(2H, m), 2.20–2.70(4H, m), 3.60(3H, s), 3.70(3H, s), 6.80 (1H, d), 7.00–7.70(6H, m), 7.48 (1H, s)ppm. |
| I | 9 | 3.73(3H, s), 3.87(3H, s), 4.86 (2H, s), 7.14(1H, d J 6Hz), 7.34(1H, d J 6Hz), 7.65(1H, s)ppm |
| I | 10 | 3.73(3H, s), 3.81(3H, s), 4.89 (2H, s), 6.83(1H, s), 7.11(1H, d J 6Hz)ppm |
| I | 11 | 2.44(3H, s), 3.72(3H, s), 4.88 (2H, s), 7.18(1H, d J 5Hz), 7.38 (1H, d J 5Hz), 8.04(1H, s)ppm |
| I | 23 | 3.61(3H, s), 3.76(3H, s), 6.72 (1H, d J 5Hz), 7.47(1H, s)ppm. |
| I | 36 | 3.64(3H, s), 3.80(3H, s), 3.82 (2H, s), 6.56(1H, s), 6.75(1H, d), 7.0–7.3(6H, m)ppm |
| I | 37 | 2.24(3H, s), 3.77(3H, s), 4.88 (2H, s), 7.11(1H, d J 5Hz), 7.38(1H, s)ppm |
| I | 39 | 3.61(3H, s), 3.85(3H, s), 6.72 (1H, d J 5Hz), 6.86(1H, s), 7.17 (1H, d J 5Hz)ppm |
| II | 1 | 3.75(3H, s), 3.90(3H, s), 7.2–7.6 (4H, m including a one proton |

TABLE VII: SELECTED PROTON NMR DATA

Table VII shows selected proton nmr data for certain compounds described in Tables I to VI. Chemical shifts are measured in ppm from tetramethylsilane, and deuterochloroform was used as solvent throughout. The following abbreviations are used:

br = broad   t = triplet
s = singlet  q = quartet
d = doublet  m = multiplet

| TABLE NO. | COMPOUND NO. | |
|---|---|---|
| II | 3 | singlet at 7.50)ppm 3.61(3H, s), 3.72(3H, s), 3.90 (2H, s), 6.72(1H, s), 7.00(1H, s) 7.12(5H, m)7.40(1H, s)ppm |
| II | 4 | 2.93(4H, s), 3.71(3H, s), 3.84 (3H, s), 6.82(1H, d J 6Hz), 7.11 (1H, d J 6Hz), 7.54(1H, s)ppm |
| II | 9 | 3.72(3H, s), 3.84(3H, s), 5.03 (2H, s), 6.88–6.96(4H, m), 7.22–7.27(3H, m), 7.57(1H, s)ppm |
| II | 39 | 3.75(3H, s), 3.90(3H, s), 6.84 (1H, d J 6Hz), 7.24(1H, d J 6Hz), 7.58(1H, s)ppm |
| II | 40 | 0.97(3H, t), 1.69(2H, sextet), 3.68(3H, s), 3.84(3H, s), 4.15 (2H, t), 7.20(1H, d J 4Hz), 7.51 (1H, s), 8.08(1H, d J 4Hz)ppm |
| III | 1 | 3.78(3H, s), 3.94(3H, s), 6.35–6.60(2H, m), 7.42(1H, m), 7.45 (1H, s)ppm |
| IV | 3 | 3.68(3H, s), 3.75(3H, s), 3.80 (2H, s), 6.30(1H, d), 7.20(5H, m), 7.30(1H, d), 7.50(1H, s)ppm |
| VI | 1 | 3.64(3H, s), 3.76(3H, s), 3.90 (3H, s), 6.54(2H, m), 7.04 (1H, m), 7.36(1H, s)ppm |
| VI | 11 | 3.17(3H, s), 3.63(3H, s), 3.75 (3H, s), 6.16(1H, m), 6.25–6.57 (2H, q, J 12Hz), 6.60(1H, m), 7.05–7.25(5H, m), 7.29(1H, s)ppm |
| VI | 58 | 3.75(6H, s), 3.83(3H, s), 6.8–7.5 (4H, m), 7.56(1H, s)ppm |
| VI | 59 | 3.70(3H, s), 3.82(3H, s), 6.56 (1H, m), 6.65(1H, m), 7.14(1H, m), 7.31(1H, s), 8.4(1H, br s)ppm |
| II | 36 | 3.72(3H, s), 3.86(3H, s), 4.06 (3H, s), 6.96(1H, d), 7.40(1H, s), 7.49(1H, d), 7.67(1H, s)ppm |
| VI | 4 | 2.76(4H, m), 3.44(3H, s), 3.73 (3H, s), 3.83(3H, s), 6.03 (1H, m), 6.56(1H, m), 7.1–7.3(5H, m), 7.51(1H, s)ppm |
| VI | 62 | 3.78(3H, s), 3.95(3H, s), 3.97 (3H, s), 7.37(1H, m), 7.42(1H, m) 7.47(1H, s), 9.53(1H, s)ppm |
| VI | 60 | 3.75(3H, s), 3.87(3H, s), 3.95 (3H, s), 6.13(1H, d J 2Hz), 6.87 (1H, d J 2Hz), 7.65(1H, s), 9.45 (1H, s)ppm |
| V | 61 | 3.80(3H, s), 4.00(3H, s), 6.15–6.30(1H, m), 6.65–6.84(2H, m), 7.40(2H, s)ppm |
| III | 4 | 2.52–2.60(2H, m), 2.78–2.85(2H, m), 3.73(3H, s), 3.88(3H, s), 6.28(2H, d), 7.39(1H, d), 7.57 (1H, s)ppm. |
| IV | 1 | 3.78(3H, s), 3.96(3H, s), 6.90 (1H, m), 7.40(1H, m), 7.48(1H, s), 7.90(1H, m)ppm. |
| V | 62 | 2.04(3H, s), 3.70(3H, s), 3.85 (3H, s), 3.82–3.95(1H, m), 4.05–4.13(1H, m), 5.80–5.88(1H, m), 6.04(1H, m), 6.12(1H, m), 6.54 (1H, m), 7.66(1H, s)ppm. |
| V | 63 | 2.07(3H, s), 3.66(3H, s), 3.80 (3H, s), 4.0–4.06(2H, m), 5.9(1H, m), 6.08(1H, m), 6.23(1H, s), 6.72 (1H, m)ppm. |
| VI | 10 | 3.68(3H, s), 3.71(3H, s), 3.83 (3H, s), 6.1(1H, m), 6.66(1H, m), 6.66(1H, d J 16Hz), 6.90(1H d J 16Hz), 7.2–7.4(5H, m), 7.50(1H, s) ppm. |

The compounds of the invention of formula (I) may be prepared by the steps shown in Schemes I to IV. Throughout these Schemes, the terms $R^1$, $R^2$, X, Y, Z, $Z^1$, W and A are as defined above, L is a halogen (iodine, bromine or chlorine), M is a metal (such as lithium) or a metal plus an associated halogen (such as MgI, MgBr or MgCl), $R^{13}$ is hydrogen or a metal (such as sodium), $R^{14}$ is alkyl and $R^{15}$ is alkyl or optionally substituted aryl. Each of the transformations shown in Schemes I to IV is performed at a suitable temperature and usually in a suitable solvent.

The compounds of formula (I) may exist as mixtures of geometric isomers which can be separated by chromatography, distillation or fractional crystallisation. The use of the formula:

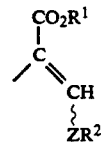

is intended to signify a separable mixture of both geometric isomers about the acrylate double bond, i.e.:

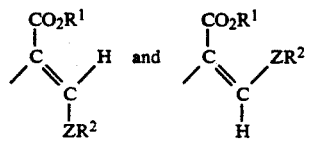

In Scheme I, compounds of formula (I) can be prepared by treatment of ketoesters of formula (II) with phosphoranes of formula (VI) in a convenient solvent such as diethyl ether (see, for example, EP-A-0044448 and EP-A-0178826. Compounds of formula (I) wherein Z is sulphur may also be prepared by treating ketoesters of formula (II) with lithio-species of formula $(CH_3)_3SiCH(Li)SR^2$ (see, for example, D J Peterson, *J. Org. Chem.*, 1968, 33, 780 and F A carey and A S Court, *J. Org. Chem.*, 1972, 37, 939).

Ketoesters of formula (II) can be prepared by treatment of metallated species (III) with an oxalate (VII) in a suitable solvent such as diethyl ether or tetrahydrofuran. The preferred method often involves slow addition of a solution of the metallated species (III) to a stirred solution of an excess of the oxalate (VII) (see, for example, L. M. Weinstock, R. B. Currie and A. V. Lovell, *Synthetic Communications,* 1981, 11, 943, and references therein).

The metallated species (III) in which M is MgI, MgBr or MgCl (Grignard reagents) can be prepared by standard methods from the corresponding halides (IV) in which L is I, Br or Cl respectively. The metallated species (III) in which M is lithium can be prepared by standard methods by treatment of the corresponding halides (IV) with an organo-lithium reagent such as n-butyl-lithium. The metallated species (III) wherein A is oxygen, sulphur or $NR^3$ in which M is a lithium atom at the 2- or 5-position can also be prepared by direct lithiation of compounds (V) using a strong lithium base such as n-butyl-lithium or lithium diisopropylamide (see, for example, H W Gschwend and H R Rodriguez, *Organic Reactions*, 1979, 26, 1).

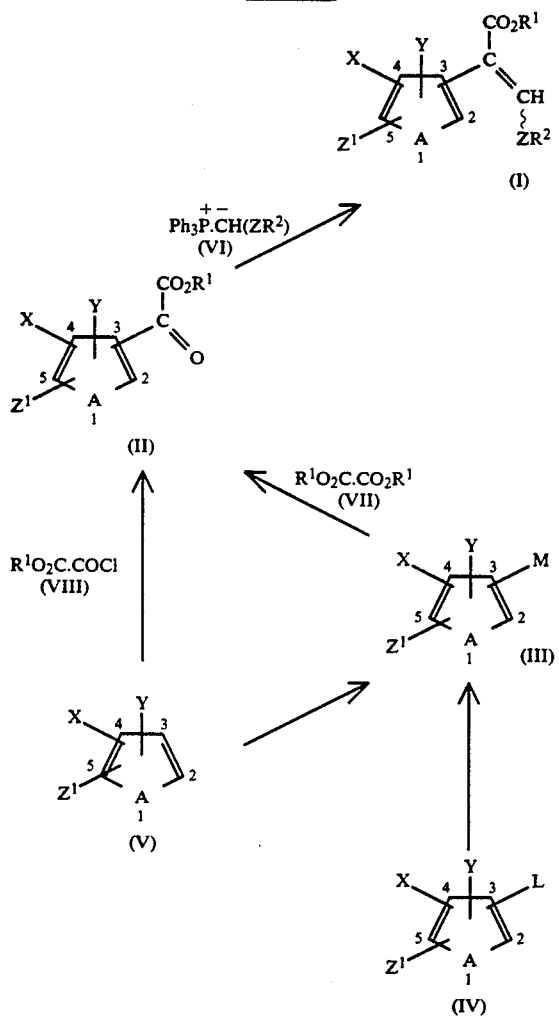

Scheme I

Alternatively, ketoesters of formula (II) can be prepared from compounds of formula (V) by treatment with acid chlorides of formula (VIII) in a suitable solvent (such as chloroform) optionally in the presence of a Lewis acid (such as aluminium chloride or boron trifluoride).

In a variation of this approach, ketoesters of formula (II) can be prepared by treatment of compounds of formula (V) with oxalyl chloride, optionally in the presence of a Lewis acid, followed by treatment of the resulting acid chloride with an alcohol of formula $R^1OH$, wherein $R^1$ is as defined above, optionally in the presence of a base such as triethylamine. The intermediate acid chloride may be isolated.

Acylations of the kind described above, that is, acylations of thiophenes, pyrroles or furans with alkyl oxalyl chlorides or with oxalyl chloride, are generally regioselective. The patterns of regioselectivity follow those described in the chemical literature for acylations of these ring systems with a variety of acid chlorides (see, for example, Comprehensive Heterocyclic Chemistry, A R Katritzky and C. W. Rees, Editors, Volume 4, Pergamon Press, 1984), and depend on the position or positions and type of substituents, if any, on the thiophene, pyrrole or furan ring undergoing acylation. Acylation is generally preferred at the 2- or the 5-positions (when one or both of these positions is unsubstituted), although particular substituents, such as benzenesulphonyl- or tri-isopropylsilyl-groups, on the nitrogen of pyrrole can direct acylation mainly to the 3- or 4-position of the ring. Many substituents at the 3-position of a thiophene, pyrrole or furan ring direct acylation preferentially to the 2-position (as opposed to the 5-position) of the ring, and examples of such substituents are (E)-styryl, phenoxymethyl- and $CH_3O_2C—C=CH—OCH_3$ groups.

Other methods for the preparation of ketoesters of formula (II) are described in the chemical literature (see, for example, D. C. Atkinson, K. E. Godfrey, B. Meek, J. F. Saville and M. R. Stillings, *J. Med. Chem.*, 1983, 26, 1353; D. Horne, J. Gaudino and W. J. Thompson, *Tetrahedron Lett.*, 1984, 25, 3529; and G. P. Axiotis, *Tetrahedron Lett.*, 1981, 22, 1509).

Compounds of general formula (IV) and (V) can be prepared by standard methods described in the chemical literature.

Alternative approaches to the compounds of the invention of formula (I) where Z is an oxygen atom are outlined in Scheme II. $R^{13}$ is hydrogen or a metal (preferably an alkali metal such as sodium or potassium) and $R^{14}$ is an alkyl group.

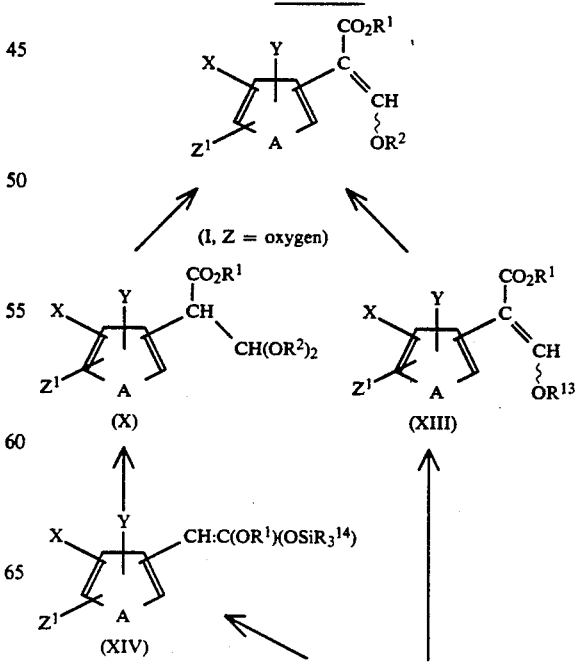

Scheme II

-continued
Scheme II

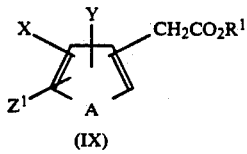

(IX)

Compounds of formula (I, Z is oxygen) can be prepared by treatment of compounds of formula (IX) with a base (such as sodium hydride or a sodium alkoxide of formula $R^1ONa$, wherein $R^1$ is as defined above) and a formic ester of formula $HCO_2R^1$, wherein $R^1$ is as defined above. If a species of formula $R^2Q$, wherein Q is a leaving group such as a halide (chloride, bromide or iodide), a $R^2SO_4$-anion, or a sulphonyloxy-anion, and $R^2$ is as defined above, is then added to the reaction mixture, compounds of formula (I, Z is oxygen) may be obtained. If a protic acid is added to the reaction mixture, compounds of formula (XIII) wherein $R^{13}$ is hydrogen are obtained. Alternatively, the species of formula (XIII) wherein $R^{13}$ is a metal may themselves be isolated from the reaction mixture.

Compounds of formula (XIII) wherein $R^{13}$ is a metal can be converted into compounds of formula (I, Z is oxygen) by treatment with a species of formula $R^2Q$, wherein $R^2$ and Q are as defined above. Compounds of formula (XIII) wherein $R^{13}$ is hydrogen can be converted into compounds of formula (I, Z is oxygen) by successive treatment with a base (such as potassium carbonate) and a species of formula $R^2Q$.

Alternatively, compounds of formula (I, Z is oxygen) can be prepared from acetals of formula (X) by elimination of the elements of the alcohol $R^2OH$, wherein $R^2$ is as defined above, under either acidic or basic conditions. Examples of reagents or reagent mixtures which can be used for this transformation are lithium di-isopropylamide; potassium hydrogen sulphate (see, for example, T. Yamada, H. Hagiwara and H. Uda, *J. Chem. Soc., Chemical Communications*, 1980, 838, and references therein); and triethylamine, often in the presence of a Lewis acid such as titanium tetrachloride (see, for example, K. Nsunda and L. Heresi, *J. Chem. Soc., Chemical Communications*, 1985, 1000).

Acetals of formula (X) can be prepared by treatment of alkyl silyl ketene acetals of formula (XIV) wherein $R^{14}$ is an alkyl group, with a trialkyl orthoformate of formula $(R^2O)_3CH$, wherein $R^2$ is as defined above, in the presence of a Lewis acid such as titanium tetrachloride (see, for example, K Saigo, M Osaki and T Mukaiyama, *Chemistry Letters*, 1976, 769).

Alkyl silyl ketene acetals of formula (XIV) can be prepared from compounds of formula (IX) by treatment with a base and a trialkylsilyl halide of formula $R^{14}_3SiCl$ or $R^{14}_3SiBr$, such as trimethylsilyl chloride, or a base (such as triethylamine) and a trialkylsilyl triflate of formula $R^{14}_3Si-OSO_2CF_3$ (see, for example, C Ainsworth, F Chen and Y Kuo, *J.Organometallic Chemistry*, 1972, 46, 59).

It is not always necessary to isolate the intermediates (XIV) and (X); under appropriate conditions, compounds of formula (I) may be prepared from compounds of formula (IX) in "one pot" by the successive addition of suitable reagents listed above.

The compounds of formula (IX) can be prepared by standard methods described in the chemical literature.

Alternative approaches to the compounds of the invention of formula (I) where Z is an oxygen atom are outlined in Scheme III.

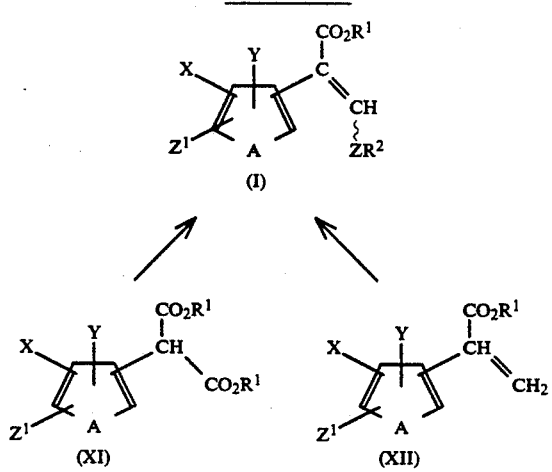

Thus partial reduction of malonate derivatives of formula (XI) with a reducing agent such as lithium aluminium hydride in a suitable solvent such as diethyl ether, followed by an aqueous or acidic work-up, gives compounds of formula (XIII) wherein $R^{13}$ is hydrogen which can be converted into compounds of formula (I, Z is oxygen) by the step shown in Scheme II and described above (see, for example, M Barczai-Beke, G Dornyei, G Toth, J Tamar and Cs Szantay, *Tetrahedron*, 1976, 32, 1153, and references therein).

In addition, compounds of formula (I) can be made from acrylic acid derivatives of formula (XII) by successive treatment with bromine, a reagent of formula $R^2OM$, wherein $R^2$ and M are as defined above, and sodium hydrogen sulphate or a related chemical (see, for example, G Shaw and R N Warrener, *Journal of the Chemical Society*, 1958, 153, and references therein).

Compounds of formulae (XI) and (XII) can be prepared by standard methods described in the chemical literature.

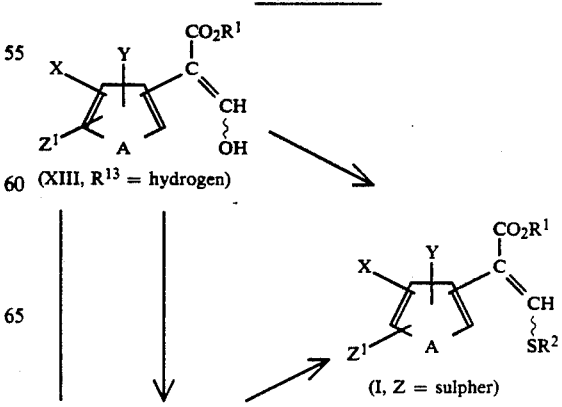

-continued
Scheme IV

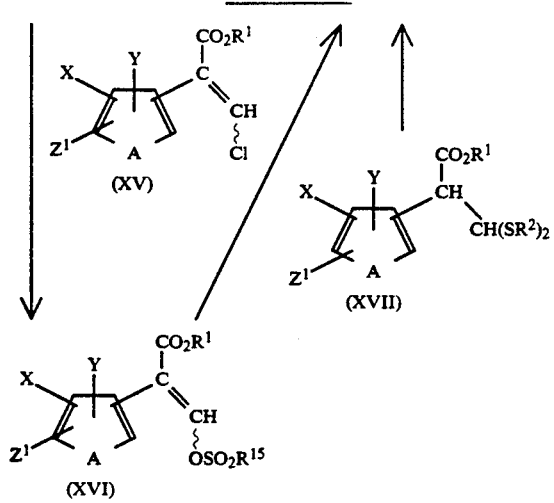

Compounds of formula (I, Z is sulphur) can be prepared from compounds of formula (XIII, $R^{13}$ is hydrogen) by the steps shown in Scheme IV, that is:

(i) From enols of formula (XIII, $R^{13}$ is hydrogen; these compounds are in equilibrium with the tautomeric formylacetates) by treatment with thiols of general formula $R^2SH$, wherein $R^2$ is defined as above, under acidic conditions, often in the presence of a dehydrating agent (see, for example, P Bernstein, *Tetrahedron Letters*, 1979, 1015).

(ii) From beta-chloroacrylates of formula (XV) by treatment with thiolates of formula $R^2SM$, wherein $R^2$ and M are defined as above. The beta-chloroacrylates (XV) can be made from enols of formula (XIII, $R^{13}$ is hydrogen) using a chlorinating reagent such as phosphorus pentachloride, often in a suitable solvent such as a chlorinated hydrocarbon.

(iii) From beta-sulphonyloxyacrylates of formula (XVI), wherein $R^{15}$ is an alkyl or an optionally substituted aryl group, by treatment with thiolates of formula $R^2SM$ wherein $R^2$ and M are defined as above. The beta-sulphonyloxyacrylates (XVI) can be made from enols of formula (XIII, $R^{13}$ is hydrogen) using a sulphonyl chloride of formula $R^{15}SO_2Cl$, wherein $R^{15}$ is defined as above, usually in the presence of a base such as pyridine or triethylamine.

(iv) From dithioacetals of formula (XVII) by elimination of the elements of the thiol $R^2SH$ under acidic or basic conditions. The dithioacetals (XVII) may be prepared by various methods described in the literature, for example, by treatment of compounds of formula (I, Z is oxygen) with an excess of the thiol $R^2SH$ under acidic conditions.

In further aspects the invention provides processes as hereindescribed for preparing the compounds of the invention and the intermediate chemicals of formulae (II) and (IX)–(XVII).

The compounds and metal complexes of the invention are active fungicides, and may be used to control one or more of the pathogens:

*Pyricularia oryzae* on rice

*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants.

*Erysiphe graminis* (powdery mildew) on barley and wheat and other powdery mildews on various hosts such as

*Sphaerotheca macularis* on hops

*Sphaerotheca fuliginea* on cucurbits (e.g. cucumber),

*Podosphaera leucotricha* on apples and *Uncinula necator* on vines.

*Helminthosporium* spp., *Rhynchosporium* spp., *Septoria* spp., *Pseudocercosporella herpotrichoides* and *Gaeumannomyces graminis* on cereals.

*Cercospora arachidicola* and *Cercosporidium personata* on peanuts and other *Cercospora* species on other hosts for example sugar beet, bananas, soya beans and rice.

*Botrytis cinerea* (grey mould) on tomatoes, strawberries, vegetables, vines and other hosts.

*Alternaria* species on vegetables (e.g. cucumber), oil seed rape, apples, tomatoes and other hosts.

*Venturia inaequalis* (scab) on apples

*Plasmopara viticola* on vines

Other downy mildews such as *Bremia lactucae* on lettuce, *Peronospora* spp. on soybeans, tobacco, onions and other hosts and *Pseudoperonospora humuli* on hops and *Pseudoperonospora cubensis* on cucurbits

*Phytophthora infestans* on potatoes and tomatoes and other *Phytophthora* spp. on vegetables, strawberries, avocado, pepper, ornamentals, tobacco, cocoa and other hosts.

*Thanatephorus cucumeris* on rice and other *Rhizoctonia* species on various hosts such as wheat and barley, vegetables, cotton and turf.

Some of the compounds have shown a broad range of activities against fungi in vitro.

They may also have activity against various post-harvest diseases of fruit (e.g. *Penicillium digitatum* and *italicum* and *Trichoderma viride* on oranges and *Gloesporium musarum* on bananas).

Further some of the compounds may be active as seed dressings against *Fusarium* spp., *Septoria* spp., *Tilletia* spp. (bunt, a seed borne disease of wheat), *Ustilago* spp., *Helminthosporium* spp. on cereals, *Rhizoctonia solani* on cotton and *Pyricularia oryzae* on rice.

The compounds may move acropetally in the plant tissue. Moreover, the compounds may be volatile enough to be active in the vapour phase against fungi on the plant.

The compounds may also be useful as industrial (as opposed to agricultural) fungicides, e.g. in the prevention of fungal attack on wood, hides, leather and especially paint films.

Some of the compounds of the invention, in particular compounds of formula (I) where A is $-NR^3$, X, Y and $Z^1$ are hydrogen and W is $R^1O_2C-C=CHZR^2$ wherein Z is oxygen and $R^1$ and $R^2$ are alkyl, exhibit insecticidal activity. Compound 38 of Table V has been found to be active against *Diabrotica balteata* (root worm larvae).

Similarly, some compounds may exhibit plant growth regulating activity and may be deployed for this purpose, at appropriate rates of application.

This invention, therefore, includes the foregoing uses of the compounds (and compositions containing them) in addition to their principal use as fungicides.

The compounds may be used directly for fungicidal purposes but are more conveniently formulated into compositions using a carrier or diluent. The invention thus provides a fungicidal composition comprising a compound of general formula (I) as hereinbefore defined, and a fungicidally acceptable carrier or diluent.

The invention also provides a method of combating fungi, which comprises applying to a plant, to seed of a plant, or to the locus of the plant or seed, a compound as hereinbefore defined, or a composition containing the same.

The compounds can be applied in a number of ways. For example they can be applied, formulated or unformulated, directly to the foliage of a plant, to seeds or to other medium in which plants are growing or are to be planted. They can be sprayed on, dusted on or applied as a cream or paste formulation, or they can be applied as a vapour or as slow release granules. Application can be to any part of the plant including the foilage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate their dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone and methylcyclohexanone, chlorinated hydrocarbons such as chlorobenzene and trichlorethane, and alcohols such as furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorous-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants eg. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carb-oxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitable 10–85%, for example 25–60%, by weight of the active ingredient. After dilution to form aqueous preparations, such preparations may contain varying amounts of the active ingredient depending upon the intended purpose, but an aqueous preparation containing 0.001% to 10% by weight of active ingredient may usually be used.

The compositions of this invention may contain other compounds having biological activity, e.g. compounds having similar or complementary fungicidal activity or plant possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil borne diseases and downy and powdery mildews on grapes and powdery mildew and scab on apple etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, 4-chloro-N-(1-cyano-1-ethoxymethyl)benzamide, benalaxyl, fosetyl-aluminium, fenarimol, iprodione, prothiocarb, procymidone, vinclozolin, penconazole, myclobutanil, propamocarb, diconazole, pyrazophos, ethirimol, ditalimfos, tridemorph, triforine, nuarimol, triazbutyl, guazatine, triacetate salt of 1,1'-iminodi-(octamethylene)diguanidine, buthiobate, propiconazole, prochloraz, flutriafol, hexaconazole, (2RS, 3RS)-2-(4-chlorophenyl)-3-cyclopropyl-1-(1H-1,2,4-triazol-1-yl)butan-2-ol, (RS)-1-(4-chlorophenyl)-4,4-dimethyl-3-(1H-1,2,4-triazol-1-ylmethyl)pentan-3-ol, flusilazole, pyrifenox, triadimefon, triadimenol, diclobutrazol, fenpropimorph, fenpropidine, chlorozolinate, imazalil, fenfuram, carboxin, oxycarboxin, methfuroxam, dodemorph, BAS 454, blasticidin S, kasugamycin, edifenphos, Kitazin P, cycloheximide, phthalide, probenazole, isoprothiolane, tricyclazole, pyroquilon, chlorobenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyimino-acetyl)-3-ethyl urea, fenapanil, tolclofos-methyl, pyroxyfur, polyram, maneb, mancozeb, captafol, chlorothalonil, anilazine, thiram, captan, folpet, zineb, propineb, sulphur, dinocap, dichlone, chloroneb, binapacryl, nitrothal-isopropyl, dodine, dithianon, fentin hydroxide, fentin acetate, tecnazene, quintozene, dicloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g. grasses).

Examples of suitable plant growth regulating compounds for use with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrate the invention. Throughout these Examples, the term "ether" refers to diethyl ether, magnesium sulphate was used to dry solutions, and reactions involving water-sensitive intermediates were performed under nitrogen and in dried solvents. Unless otherwise stated, chromatography was performed using silica gel as the stationary phase. Where shown, infrared and nmr data are selective; no attempt is made to list every absorption. Unless otherwise stated, nmr spectra were recorded in deuterochloroform. The following abbreviations are used throughout:

| | | | |
|---|---|---|---|
| DMSO = | dimethylsulphoxide | delta = | chemical shift |
| THF = | tetrahydrofuran | $CDCl_3$ = | deuterochloroform |
| DMF = | N,N-dimethylformamide | s = | singlet |
| GC = | gas chromatography | d = | doublet |
| MS = | Mass spectrum | nmr = | nuclear magnetic resonance |
| HPLC = | high performance liquid chromatography | t = | triplet |
| mp = | melting point | m = | multiplet |
| IR = | infrared | J = | coupling constant |
| mmol = | millimole | Hz = | Hertz |
| mmHg = | pressure in millimeters of mercury | br = | broad |
| mg = | milligramme(s) | | |
| g = | gramme(s) | | |

EXAMPLE 1

This Example illustrates the preparation of the (E)- and (Z)-isomers of methyl 2-(3-benzyl-2-thienyl)-3-methoxypropenoate (compounds number 36 and 3 of Table I).

A solution containing $P_2I_4$ (3.42 g, 6 mmol) and 3-(1-hydroxybenzyl)thiophene (1.90 g, 10 mmol) in sodium-dried toluene (100 ml) was heated under nitrogen for one hour. The reaction mixture was cooled and then quenched with 10% aqueous sodium sulphite. The mixture was extracted with ether, and the combined organic phases were washed with water and brine then dried. Filtration and evaporation afforded a yellow oil, which on bulb-to-bulb distillation (110° C. at 0.05 mmHg) gave a pale-pink oil. Chromatography with dichloromethane gave 3-benzylthiophene as an oil (1.02 g, 53% yield); ¹H nmr:delta 3.84 (2H,s), 7.0-7.2 (8H,m) ppm.

A solution of 3-benzylthiophene (1.0 g, 5.75 mmol) and methyl oxalyl chloride in dry dichloromethane (50 ml) was added to a stirred suspension of aluminum chloride (1.35 g) in dry dichloromethane (50 ml) over a period of 40 minutes with ice cooling. After stirring at room temperature for 2 hours, the reaction mixture was poured onto ice and acidified with dilute hydrochloric acid. The aqueous layer was separated and extracted with dichloromethane and then the combined organic layers were washed with water and brine and dried. Filtration and evaporation under reduced pressure afforded a yellow oil (1.63 g) which was chromatographed (eluent 30% ether in petrol) to give methyl 2-(3-benzyl-2-thienyl)-2-oxoacetate (240 mg); ¹H nmr: delta 3.90 (3H,s), 4.40 (2H,s), 6.90 (1H, d, J=4.2 Hz), 7.2-7.4 (5H,m), 7.6 (1H, d, J=4.2 Hz) ppm; and methyl 2-(4-benzyl-2-thienyl)-2-oxoacetate (50 mg), ¹H nmr: delta 3.90 (3H,s), 3.99 (2H,s), 7.0-7.3 (6H,m), 7.95 (1H, d, J=1.3 Hz) ppm.

To a suspension of (methoxymethyl)triphenylphosphonium chloride and sodamide (0.4 g of a 1:1 molar mixture) in dry THF was added a solution of methyl 2-(3-benzyl-2-thienyl)-2-oxoacetate (220 mg, 0.8 mmol) in dry THF (5 ml). The reaction mixture was stirred at room temperature for 30 minutes. More (methoxymethyl)triphenylphosphonium chloride and sodamide (0.2 g of a 1:1 molar mixture) were added and stirring was continued for a further one hour. The reaction mixture was poured into water and then extracted with ether. The combined ether layers were washed with water and brine and then dried. Filtration through a pad of silica gel to remove triphenylphosphine oxide, followed by HPLC (eluent dichloromethane) afforded (Z)-methyl 2-(3-benzyl-2-thienyl)-3-methoxypropenoate, an oil (100 mg), ¹H nmr: delta 3.64 (3H, s), 3.78 (6H,s), 6.75 (1H,d), 7.0-7.4 (6H,m), 7.60 (1H,s) ppm; and (E)-methyl 2-(3-benzyl-2-thienyl)-3-methoxypropenoate, an oil (30 mg), ¹H nmr: delta 3.64 (3H,s), 3.80 (3H,s), 3.82 (3H,s), 6.56 (1H,s), 6.75 (1H,d), 7.0-7.3 (6H,m) ppm.

EXAMPLE 2

This Example illustrates the preparation of (E)-methyl 3-methoxy-2-(3-thienyl)propenoate (compound number 1 of Table II).

Methyl 3-thienylacetate was prepared by heating 3-thienylacetic acid in acidic methanol. It is an oil, ¹H nmr: delta 3.71 (2H, s), 3.76 (3H, s) ppm.

A solution of methyl 3-thienylacetate (23.8 g) in methyl formate (94 ml) and DMF (30 ml) was added dropwise to a stirred suspension of sodium hydride (7.30 g) in DMF (250 ml) at a temperature between 0° and 10° C. (effervescence). Following the addition, the reaction mixture was allowed to stir at room temperature for 30 minutes. It was then poured into water and the resulting mixture was acidified with dilute hydrochloric acid, then extracted with ether. The extracts were washed with water, dried and concentrated to give an orange oil (28.80 g). Potassium carbonate (42.0 g) and, after 15 minutes, dimethyl sulphate (13.62 ml) were added successively to a stirred solution of this orange oil in DMF (250 ml). After 2 hours at room temperature, the mixture was diluted with water and extracted with ether. The extracts were washed with water, dried and concentrated to give an orange oil (22.50 g) which was distilled (short path distillation apparatus) to give the title compound (20.60 g, 68% yield from methyl 3-thienylacetate) as a colourless liquid. ¹H nmr: see Table VII.

EXAMPLE 3

This Example illustrates the preparation of (E)-methyl 2-(2-formyl-3-thienyl)-3-methoxypropenoate (compound number 37 of Table II).

Phosphorus oxychloride (4.70 ml) was added in one portion to vigorously-stirred DMF (4.30 ml), cooled in an ice bath. The resulting mixture thickened, and it was diluted with dichloromethane (10 ml), then stirred at room temperature for 30 minutes. A solution of (E)-methyl 3-methoxy-2-(3-thienyl)propenoate (10.0 g, prepared as described in Example 2) in dichloromethane (25 ml) was then added dropwise at room temperature over 5 minutes. The resulting mixture was stirred at room temperature for 5 hours, then poured into saturated aqueous sodium acetate (250 ml) and heated on a steam bath until a white solid separated, and then for a further 10 minutes. The whole mixture was extracted with ethyl acetate. The extracts were washed with water, dried and concentrated to give an oily solid which was triturated with ether, filtered off and dried to give the title compound (9.20 g, 81% yield) as a solid, mp 144°-145° C. An analytical sample, recrystallised from ethyl acetate, had melting point 147°-147° C. ¹H nmr: delta 3.76 (3H, s), 3.89 (3H, s), 7.06 (1H, d J 5 Hz), 7.66 (1H, d J 5 Hz), 7.72 (1H, s), 9.72 (1H, s) ppm.

EXAMPLE 4

This Example illustrates the preparation of (E)-methyl 2-(2-benzoyl-3-thienyl)-3-methoxypropenoate (compound number 24 of Table II).

Powdered aluminium chloride (1.34 g) was added in portions to a stirred solution of (E)-methyl 3-methoxy-2-(3-thienyl)propenoate (1.00 g, prepared as described in Example 2) and benzoyl chloride (0.78 g) in dichloromethane (10 ml), cooled in an ice bath. Following the addition, the mixture was stirred at room temperature for 4 hours, then extracted with ether. The extracts were washed with dilute hydrochloric acid (X1), then with water (X3), then dried and concentrated to give a dark orange oil (0.82 g) which was chromatographed using a 1:1 mixture of ethyl acetate and petrol as eluant to give (i) (E)-methyl 2-(2-benzoyl-4-thienyl)-3-methoxypropenoate (100 mg, 7% yield) as an oil, ¹H nmr: delta 3.76 (3H, s), 3.92 (3H, s) ppm; and (ii) methyl 2-(2-benzoyl-3-thienyl)-3-hydroxypropenoate [in tautomeric equilibrium with methyl (2-benzoyl-3-thienyl)formylacetate] (220 mg, 15% yield) as a gum, ¹H nmr: delta 3.61 (3H, s), 7.01 (1H, d J 5 Hz), 7.57 (1H, d J 5 Hz), 11.76 (1H, d J 13 Hz) ppm.

Potassium carbonate (144 mg) and, after 15 minutes, dimethyl sulphate (0.046 ml) were added to a stirred solution of part of the methyl 2-(2-benzoyl-3-thienyl)-3-hydroxypropenoate (150 mg) in DMF (3 ml). After 2 hours at room temperature, the mixture was diluted with water and extracted with ether. The extracts were washed with water, dried and concentrated to give the title compound (120 mg, 81% yield) as a fawn solid, mp 95°-96° C. An analytical sample, recrystallised from ethyl acetate, had mp 96°-97° C.; ¹H nmr: delta 3.63 (3H, s), 3.73 (3H, s), 7.12 (1H, d J 5 Hz), 7.16 (1H, s), 7.56 (1H, d J 5 Hz) ppm.

EXAMPLE 5

This Example illustrates the preparation of (Z)- and (E)-isomers of methyl 3-methoxy-2-(3-phenoxymethyl- 2-thienyl)propenoate (compounds numbers 9 and 10 respectively of Table I).

A solution of methanesulphonyl chloride (20.3 ml) in dichloromethane (20 ml) was added dropwise over 15 minutes to a stirred solution of 3-(hydroxymethyl)thiophene (20.0 g) and triethylamine (42.8 ml) in dichloromethane (150 ml), cooled in an ice bath. The solution, initially colourless, became yellow and a white solid precipitated. After 1 hour at ice bath temperatures the reaction mixture was allowed to warm to room temperature and was stirred for 2 hours. The mixture was then washed successively with water, dilute hydrochloric acid, water, aqueous sodium bicarbonate and aqueous sodium chloride, then dried and concentrated to give 3-(chloromethyl)thiophene (14.50 g, 63% yield) as a yellow liquid, $^1$H nmr: delta 4.62 (2H, s) ppm.

A solution of phenol (13.16 g) in DMF (10 ml) was added in portions over 10 minutes to a stirred suspension of sodium hydride (3.12 g) in DMF (100 ml). After 2 hours, a solution of 3-(chloromethyl)thiophene (14.50 g) in DMF (30 ml) was added in one portion and the resulting mixture was stirred at room temperature for 3 hours then poured into water and extracted with ether. The extracts were washed successively with water, dilute aqueous sodium hydroxide, and aqueous sodium chloride, then dried and concentrated to give 3-(phenoxymethyl)thiophene (18.86 g, 91% yield) as a white solid. An analytical sample, recrystallised from methanol, had mp 49°–50° C.

n-Butyl-lithium (11.56 ml of a 2.5M solution in n-hexane) was added dropwise to a stirred solution of 3-(phenoxymethyl)thiophene (5.0 g) in THF (50 ml) at a temperature of about −70° C. Following the addition, the reaction mixture was allowed to warm to room temperature and stir for 1 hour. It was then added dropwise to a stirred solution of dimethyl oxalate (6.2 g) in THF (75 ml) at a temperature of about −10° C. The resulting mixture was stirred for 2 hours at room temperature, then poured into water and extracted with ether. The extracts were washed with water, dried, concentrated and chromatographed using a 1:1 mixture of ether and petrol as eluent to give an orange oil (2.71 g) which crystallised on standing. This solid was triturated with petrol, filtered off and dried to give methyl 2-(3-phenoxymethyl-2-thienyl)-2-oxoacetate (770 mg, 11% yield) as a yellow solid, mp 98°–99° C., $^1$H nmr: delta 3.97 (3H, s), 5.47 (2H, s) ppm.

Potassium tert-butoxide (844 mg) was added in one portion to a stirred suspension of (methoxymethyl)triphenylphosphonium chloride (2.86 g) in ether (30 ml). The reaction mixture became red. After 20 minutes, a solution of methyl 2-(3-phenoxymethyl-2-thienyl)-2-oxoacetate (770 mg) in THF (10 ml) was added in one portion and the red colour was discharged. The resulting mixture was stirred at room temperature for 30 minutes then poured into water. The organic and aqueous layers were separated, and the latter was extracted with ether. The combined organic layers were washed with water, dried, concentrated and chromatographed using a 1:1 mixture of ether and petrol as eluent to give (i) the (Z)-isomer of the title compound (230 mg, 27%) as a pale yellow oil, IR (film) 1710, 1625 cm$^{-1}$, $^1$H nmr: see Table VII; and (ii) the (E)-isomer of the title compound (80 mg, 9% yield), also a pale yellow oil, IR (film) 1700, 1620 cm$^{-1}$, $^1$H nmr: see Table VII.

EXAMPLE 6

This Example illustrates the preparation of the (E)- and (Z)-isomers of methyl 3-(methylthio)-2-(3-phenoxymethyl-2-thienyl)propenoate (compounds numbers 37 and 11 of Table I respectively).

Potassium tert-butoxide (0.49 g) was added in one portion to a stirred solution of (methylthiomethyl)triphenylphosphonium chloride (1.82 g) in ether (30 ml). The resulting mixture became lemon yellow. After 30 minutes, a solution of methyl 2-(3-phenoxymethyl-2-thienyl)-2-oxoacetate (0.80 g, prepared as described in Example 5) in THF (10 ml) was added in one portion. The resulting mixture was stirred for 30 minutes then poured into water. The organic and aqueous layers were separated, and the latter was extracted with ether. The combined organic layers were washed with water, dried, concentrated and chromatographed using 20% ether in petrol as eluent to give (i) the (E)-isomer of the title compound (89 mg) as an oil, containing 12% of the starting ketoester by GC, $^1$H nmr: see Table VII; and (ii) the (Z)-isomer of the title compound (240 mg) as an oil, $^1$H nmr: see Table VII.

EXAMPLE 7

This Example illustrates the preparation of (E)-methyl 3-methoxy-2-[4-(prop-1-yloxycarbonyl)-3-thienyl]propenoate (compound number 40 of Table II).

Methyl (4-carboxy-3-thienyl)acetate was prepared from 4-bromothiophen-3-carboxylic acid and methyl acetoacetate by the method described by D E Ames and O. Ribeiro, J. Chem. Soc., Perkin I, 1975, 1390, for the preparation of the corresponding ethyl ester. It is a solid which, after crystallisation from aqueous methanol, had mp 121°–122° C., $^1$H nmr: delta 3.72 (3H, s), 3.95 (2H, s), 7.18 (1H, d J 3 Hz), 8.27 (1H, d J 3 Hz) ppm.

Potassium carbonate (670 mg) and, after 15 minutes, 1-iodopropane (0.26 ml) were added successively to a stirred solution of methyl (4-carboxy-3-thienyl)acetate (490 mg) in DMF (10 ml). After 3 h, the resulting mixture was diluted with water and extracted with ether. The extracts were washed with water, dried, and concentrated to give methyl [4-(prop-1-yloxycarbonyl)-3-thienyl]acetate (600 mg, quantitative yield) as a yellow liquid, pure by GC, IR (film): 1735, 1710 cm$^{-1}$, $^1$H nmr: delta 1.00 (3H, t), 1.75 (2H, q), 3.69 (3H, s), 3.92 (2H, s), 4.20 (2H, t), 7.13 (1H, d J 3.5 Hz), 8.12 (1H, d J 3.5 Hz) ppm.

Triethylamine (0.34 ml) and trimethylsilyl triflate (0.47 ml) were added successively to a stirred solution of methyl [4-(prop-1-yloxycarbonyl)-3-thienyl]acetate (600 mg) in ether (7.5 ml), cooled to 0° C. The resulting mixture was stirred over-night at room temperature, during which time a red oil precipitated. The ethereal solution was decanted from this red oil to give 'Solution A'. Titanium tetrachloride (0.27 ml) was added dropwise to a stirred solution of trimethylorthoformate (0.27 ml) in dichloromethane (10 ml), cooled to −70° C., to give a yellow suspension. 'Solution A' was then added dropwise over 10 minutes with stirring to this suspension, cooled to −70° C. The resulting mixture was allowed to warm and was stirred at room temperature over-night, then was diluted with aqueous potassium carbonate and extracted with ether. The extracts were washed with water, dried and concentrated to give an orange oil (450 mg) consisting mainly of the title compound and the starting acetate (62% and 31% respectively by GC). HPLC using a 1:1 mixture of ether and petrol on silica gel then gave the pure title compound (202 mg, 29% yield) as an almost colourless oil, IR (film): 1710, 1635 cm$^{-1}$, $^1$H nmr: see Table VII.

EXAMPLE 8

This Example illustrates the preparation of (E,E)-methyl 3-methoxy-2-(3-styryl-2-furyl)propenoate (compound number 17 of Table III).

Potassium tert-butoxide (35.7 g) was added in one portion to a stirred suspension of benzyltriphenylphosphonium chloride (41.6 g) in ether (1 liter). After 1 hour, a solution of 3-formylfuran (17.5 g) in ether (60 ml) was added to the resulting orange mixture which was then stirred for 2 hours, poured into water, and extracted with ether. The extracts were washed with water, dried and concentrated to give a solid. Trituration of this solid with ether enabled much of the weakly-soluble triphenylphosphine oxide and excess phosphonium salt to be separated, and the ether-soluble fraction (37.06 g) was chromatographed using ether as eluent to give a mixture of (E)- and (Z)-isomers of 3-styrylfuran (27 g) as a yellow solid. Crystallisation twice from methanol gave (E)-3-styrylfuran (5.12 g), mp 96° C., as a yellow solid.

A solution of methyl oxalyl chloride (4.05 g) in THF (35 ml) was added dropwise over 15 minutes to a stirred solution of (E)-3-styrylfuran (5.12 g) in THF (50 ml). Two drops of boron trifluoride etherate were added, and the resulting mixture was heated at 60° C. for 44 hours, allowed to cool, poured into water and extracted with ether. The extracts were washed with water, dried and concentrated to give a dark oily solid which was triturated with ether to give, after filtration and drying, (E)-methyl 2-(3-styryl-2-furyl)-2-oxoacetate (1.65 g, 21% yield) as a yellow solid, mp 116° C., IR (nujol) 1735 cm$^{-1}$.

(E)-Methyl 2-(3-styryl-2-furyl)-2-oxoacetate was converted into the title compound (41% yield) using the ylide from (methoxymethyl)triphenylphosphonium chloride and potassium tert-butoxide by the method described in Example 5. The title compound, a white solid, had mp 107° C., $^1$H nmr: delta 3.76 (3H, s), 3.92 (3H, s), 6.66–6.83 (3H, m), 7.18–7.48 (6H, m), 7.70 (1H, s) ppm.

EXAMPLE 9

This Example illustrates the preparation of (E)-methyl 2-(3-furyl)-3-methoxypropenoate (compound number 1 of Table IV).

A mixture of 3-formylfuran (5.0 g), methyl (methylthiomethyl)sulphoxide (7.1 g) and Triton B [(40 weight % solution of benzyltrimethylammonium hydroxide in methanol) 4.8 g] in THF (7 ml) was heated under reflux for 5 hours. After cooling, it was poured into water and extracted with ether. The extracts were washed with water (×3) and then with aqueous sodium chloride, then dried and concentrated to give a brown oil (4.0 g), IR (film) 1610, 1060 cm$^{-1}$. Acetyl chloride (1.4 ml) was added carefully with stirring to dry methanol (25 ml), cooled to 0° C. Following the addition, the resulting mixture was allowed to warm to room temperature, and part of the brown oil (2.0 g) was added to it in one portion with stirring. After 30 minutes, the resulting mixture was heated at 100° C. under reflux for 2 hours, then allowed to cool, poured into water and extracted with ether. The extracts were washed successively with water (×3), aqueous sodium bicarbonate and aqueous sodium chloride, then dried, concentrated, and eluted through a short column of silica gel using a 1:1 mixture of ether and petrol to give methyl (3-furyl)acetate (1.3 g, 36% yield from 3-formylfuran) as a yellow oil, IR (film) 1736 cm$^{-1}$.

The methyl (3-furyl)acetate was converted into the title compound in 2 steps as described in Example 2, that is (i) by reaction with sodium hydride and methyl formate, and (ii) treatment of the resulting formylacetate with potassium carbonate and dimethyl sulphate. The title compound, a yellow oil, has IR (film) 1705, 1628 cm$^{-1}$ and $^1$H nmr as shown in Table VII.

EXAMPLE 10

This Example illustrates the preparation of (E)-methyl 2-(2-formyl-3-furyl)-3-methoxypropenoate (compound number 37 of Table IV).

(E)-Methyl 2-(3-furyl)-3-methoxypropenoate, prepared as described in Example 9, was converted into the title compound (56% yield) by treatment with the Vilsmeier reagent as described for the corresponding thiophene in Example 3. The title compound is a solid, mp 124° C., IR (nujol) 1685, 1625 cm$^{-1}$, $^1$H nmr: delta 3.77 (3H, s), 3.93 (3H, s), 6.59 (1H, d J 1.5 Hz), 7.62 (1H, d J 1.5 Hz), 7.68 (1H, s), 9.59 (1H, s) ppm.

EXAMPLE 11

This Example illustrates the preparation of (E)-methyl 2-(1-benzyl-5-methylpyrrol-2-yl)-3-methoxypropenoate (compound number 57 of Table V).

To a solution of potassium tert-butoxide (1.34 g, 12 mmol) in DMF (30 ml) was added dropwise a solution of methyl (5-methylpyrrol-2-yl)oxoacetate (2.0 g, 12 mmol) in DMF (5 ml). The reaction mixture was stirred for 2 hours, cooled to 0° C., and then treated dropwise with a solution of benzyl chloride (1.4 ml, 12 mmol) in DMF (5 ml). The mixture was stirred for 6 hours, poured into water (150 ml) and then extracted with ether (2×100 ml). The organic layers were washed with brine (2×50 ml), dried and then evaporated under reduced pressure to give an orange oil. Chromatography (eluent diethyl ether-hexane 1:1) gave methyl (1-benzyl-5-methylpyrrol-2-yl)oxoacetate (2.0 g) as a yellow oil, $^1$H nmr: delta 2.22 (3H,s), 3.87 (3H,s), 5.65 (2H,s), 6.1 (1H,d), 7.9 (2H,d), 7.2–7.4 (4H,m) ppm.

A mixture of (methoxymethyl)triphenylphosphonium chloride and sodium amide (3.41 g of a 1:1 molar mixture) was stirred in THF (90 ml) at 0° C. under an atmosphere of nitrogen for 3 hours. A solution of methyl 2-(1-benzyl-5-methyl-pyrrol-2-yl)oxoacetate (1 g) in THF (5 ml) was then added dropwise at 0° C. and the resulting mixture was stirred for 16 hours. Water (5 ml) was then added and the THF was removed under reduced pressure. The residue was extracted with ether (150 ml) which was then washed with brine and dried. Evaporation under reduced pressure gave an orange oil which was chromatographed (eluent etherhexane 1:1) to give the title compound (0.35 g) as a pale yellow solid, m.p. 102°–3° C., $^1$H nmr: delta 2.12 (3H,s), 3.58 (3H,s), 3.71 (3H,s), 4.90 (2H,s), 6.04 (2H,m), 6.9 (2H,m), 7.2 (3H,m), 7.52 (1H,s) ppm.

EXAMPLE 12

This Example illustrates the preparation of (E)-methyl 3-methoxy-2-(1-methylpyrrol-2-yl)propenoate (compound number 38 of Table V).

Sodium hydride (3.05 g, 50% dispersion in oil, 64 mmol) was washed with 40°–60° C. petroleum ether and then suspended in dry DMF (30 ml) under an atmosphere of nitrogen. A solution of methyl (1-methylpyrrol-2-yl)acetate (5 g, 32 mmol) and methyl formate (39.5 ml, 64 mmol) in DMF (10 ml) was then added dropwise at room temperature with vigorous stirring. After 3 hours, the reaction mixture was poured into 10% aqueous potassium carbonate (100 ml) and extracted with ether (2×100 ml). The aqueous layer was treated with concentrated hydrochloric acid and re-extracted with ether (2×100 ml). The combined ether layers were dried and evaporated to give methyl 3-hydroxy-2-(1-methylpyrrol-2-yl)propenoate (5.4 g) as an orange oil which was used without further purification.

A solution of methyl 3-hydroxy-2-(1-methylpyrrol-2-yl)propenoate (5.4 g, 30 mmol) in DMF (10 ml) was added dropwise to a stirred solution of potassium carbonate (8.24 g, 60 mmol) in DMF (75 ml). After stirring for 2 hours at room temperature, dimethyl sulphate (2.8 ml, 29 mmol) was added dropwise and stirring was continued for a further 6 hours. The reaction mixture was poured into saturated aqueous sodium bicarbonate and then extracted with diethyl ether (2×100 ml). The combined organic layers were washed with brine, dried, and then evaporated under reduced pressure to give a viscous orange oil. Chromatography (eluent ether-hexane 1:1) gave the title compound (450 mg) as a pale yellow crystalline solid; mp 58° C.; $^1$H nmr: delta 3.45 (3H,s), 3.72 (3H,s), 3.86 (3H,s), 6.08 (1H,m), 6.17 (1H,m), 6.67 (1H,m), 7.62 (1H,s) ppm.

EXAMPLE 13

This Example illustrates the preparation of (E)-methyl 3-methoxy-2-[N-(2-phenylethyl)pyrrol-2-yl]propenoate (compound number 34 of Table V).

Pyrrole (5.00 g) was added dropwise over 5 minutes to a stirred mixture of potassium tert-butoxide (9.20 g) and 18-crown-6 (1.96 g) in ether (250 ml). Thirty minutes later, phenethyl bromide (15.16 g) was added and the resulting mixture was stirred overnight, then poured into water and extracted with ether. The extracts were washed with water, dried and concentrated to give a red liquid (22.4 g) which, on short path distillation, gave N-(2-phenylethyl)pyrrole (1.23 g) as a pale yellow liquid (oven temperature 170° C., pressure ca. 10 mmHg), containing 10% phenethyl bromide by GC, $^1$H nmr: delta 3.04 (2H, t), 4.10 (2H, t), 6.12 (2H, m), 6.60 (2H, m) ppm.

Solutions of pyrrole (0.51 g) in dichloromethane (5 ml) and, after 15 minutes, N-(2-phenylethyl)pyrrole (1.00 g) in dichloromethane (5 ml) were added dropwise to a stirred solution of methyl oxalyl chloride (0.79 g) in dichloromethane (10 ml), cooled to −70° C. After an hour at −70° C., the reaction mixture was allowed to warm to room temperature, then poured into water and extracted with ether. The extracts were washed successively with water, dilute hydrochloric acid, water, aqueous sodium bicarbonate, and aqueous sodium chloride, then dried, concentrated and chromatographed using a 1:1 mixture of ether and petrol as eluent to give methyl 2-[N-(2-phenylethyl)pyrrol-2-yl]-2-oxoacetate (0.94 g, 63% yield) as a pale yellow oil, IR (film): 1735, 1640 cm$^{-1}$, $^1$H nmr: delta 3.02 (2H, t), 3.95 (3H, s), 4.51 (2H, t) ppm.

This alpha-ketoester was converted into the title compound (24% yield) using the phosphorane derived from (methoxymethyl)triphenylphosphonium chloride and potassium tert-butoxide under the conditions described in Example 5. The title compound is a solid, mp 72°-73° C., $^1$H nmr: delta 2.94 (2H, t), 3.72 (3H, s), 3.86 (3H, s), 3.91 (2H, t), 6.06 (1H, m), 6.18 (1H, m), 6.64 (1H, m), 7.66 (1H, s) ppm.

EXAMPLE 14

This Example illustrates the preparation of (E)-methyl 3-methoxy-2-(N-methylpyrrol-3-yl)propenoate (compound number 1 of Table VI).

Pyrrole (2.9 ml, 42 mmol) was added dropwise with stirring at room temperature to a suspension of potassium tert-butoxide (4.66 g, 42 mmol) and 18-crown-6 (0.2 g, 0.76 mmol) in ether (300 ml). After 1 hour tri-isopropylsilyl chloride (8.0 g, 42 mmol) was added dropwise, and then the reaction mixture was stirred for 16 hours, and filtered. The residue was washed with ether and the combined filtrate and washings were washed with brine, then dried and concentrated to give N-tri-isopropylsilylpyrrole (8.0 g, 86% yield) as a clear oil, $^1$H nmr: delta 1.04 (18H, d), 1.38 (3H, m), 6.22 (2H, m), 6.72 (2H, m) ppm.

A solution of pyridine (10.9 ml, 135 mmol) in dichloromethane (50 ml) was added with stirring to a solution of methyl oxalyl chloride (12.4 ml, 135 mmol) in dichloromethane (200 ml) cooled to −60° C. The reaction mixture was stirred for 15 minutes then a solution of N-tri-isopropylsilylpyrrole (10.0 g, 45 mmol) in dichloromethane (10 ml) was added dropwise, still keeping the reaction mixture at −60° C. The reaction mixture was stirred for 2 days then treated with 0.5 molar hydrochloric acid (100 ml). The organic phase was separated and washed with brine, dried and concentrated to give a viscous brown oil [IR (thin film) 1730, 1660 cm$^{-1}$], which was dissolved in THF and treated with tetrabutylammonium fluoride (25 ml, 25 mmol, 1.0M solution in THF). After 10 minutes, the reaction mixture was concentrated and then partitioned between water and ethyl acetate. The organic phase was washed with brine then dried and concentrated to give a semicrystalline material, which was recrystallised from a mixture of 60°-80° C. petrol and chloroform to give methyl pyrrol-3-yloxoacetate as a light brown solid (3.3 g, 50% yield), mp 112° C., IR (nujol-mull) 2800, 1735, 1620 cm$^{-1}$, $^1$H nmr: delta 3.92 (3H, s), 6.79 (2H, m), 7.82 (1H, m), 10.7 (1H, br s) ppm.

A solution of methyl pyrrol-3-yloxoacetate (3.3 g, 22 mol) in THF (70 ml) was added at room temperature to a stirred suspension of potassium tert-butoxide (2.7 g, 24 mmol) and 18-crown-6 (0.1 g, 0.39 mmol) in ether (250 ml). The reaction mixture was stirred for 30 minutes then iodomethane (1.6 ml, 26 mmol) in ether (50 ml) was added dropwise. The reaction mixture was stirred for 16 hours then filtered through hyflo supercell and washed with brine, dried and concentrated to give methyl N-methylpyrrol-3-yloxoacetate (2.84 g, 79% yield) as a clear oil, IR (thin film) 1725, 1645 cm$^{-1}$, $^1$H nmr:delta 3.64 (3H, s), 3.85 (3H, s), 6.5 (1H, m) 6.7 (1H, m), 7.6 (1H, m) ppm.

A suspension of sodium hydride (0.815 g, 35 mmol) in DMSO (30 ml) was heated at 75° C. for 1 hour and was then diluted with THF (30 ml) and cooled in an ice bath. A solution of (methoxymethyl)triphenylphosphonium chloride (12.8 g, 34 mmol) in DMSO (25 ml) was added and the reaction mixture exothermed to 20° C. and became a dark red colour. A solution of methyl N-methylpyrrol-3-yloxoacetate (2.84 g, 17 mmol) in DMSO (10 ml) was added and the reaction mixture was stirred at room temperature for 1 hour then poured into brine (150 ml) and extracted with ethyl acetate (2×150 ml). The organic phase was washed with brine, dried and concentrated to give an orange oil which was purified by HPLC using ether as the eluent to give the title compound (1.57 g, 47% yield) as a clear pale yellow oil, IR (thin film) 1715, 1640 cm$^{-1}$, $^1$H nmr:see Table VII.

EXAMPLE 15

This Example illustrates the preparation of (E)-methyl 3-methoxy-2-(N-methyl-2-formylpyrrol-4-yl)propenoate and (E)-methyl 3-methoxy-2-(N-methyl-2-formylpyrrol-3-yl)propenoate (compounds numbers 60 and 62 of Table VI respectively).

A solution of (E)-methyl 3-methoxy-2-(N-methylpyrrol-3-yl)propenoate (1.82 g, 9.3 mmol, prepared as described in Example 14) in 1,2-dichloroethane (25 ml) was added dropwise with stirring at room temperature to the mixture resulting from adding phosphoryl chloride (1.74 ml, 18.7 mmol) to DMF (1.45 ml, 18.7 mmol) whilst cooling in ice. After stirring for 3 hours at room temperature, a saturated aqueous solution of sodium acetate (70 ml) was added and the resulting mixture was heated at reflux for 20 minutes. The mixture was cooled then extracted with dichloromethane (2×100 ml). The extracts were washed with water, dried and concentrated to give an orange oil which was purified by HPLC on silica gel using ether as eluent to give (i) (E)-methyl 3-methoxy-2-(N-methyl-2-formylpyrrol-4-yl)propenoate (0.43 g, 21% yield) as a clear oil, $^1$H nmr: see Table VII, eluted first, and (ii) (E)-methyl 3-methoxy-2-(N-methyl-2-formylpyrrol-3-yl)-propenoate (1.43 g, 69% yield) as a crystalline solid, mp 82°–84° C., $^1$H nmr: see Table VII, eluted second.

EXAMPLE 16

This Example illustrates the preparation of (E)-methyl 3-methoxy-2-(N-methyl-2-(Z)-styrylpyrrol-3-yl)-propenoate (compound number 11 of Table VI).

A suspension of sodium hydride (0.215 g, 9 mmol) in DMSO was heated at 75° C. for 1 hour, allowed to cool, and was then diluted with dry THF (20 ml) and cooled in an ice bath. Benzyltriphenylphosphonium chloride (3.5 g, 9 mmol) was added with stirring and the resulting bright red mixture was stirred for 10 minutes, then a solution of (E)-methyl 3-methoxy-2-(N-methyl-2-formylpyrrol-3-yl)-propenoate (1.0 g, 4.5 mmol, prepared as described in Example 15) in THF (20 ml) was added. The reaction mixture was stirred for 3 hours, then poured into brine (100 ml) and extracted wtih ethyl acetate (2×200 ml). The extracts were washed with brine, dried and concentrated to give an orange oil which was purified by HPLC on silica gel using ether as the eluent to give the title compound as a yellow oil (0.75 g, 56% yield) $^1$H nmr:see Table VII.

The following are examples of compositions suitable for agricultural and horticultural purposes which can be formulated from the compounds of the invention. Such compositions form another aspect of the invention. Percentages are by weight.

EXAMPLE 17

An emulsifiable concentrate is made up by mixing and stirring the ingredients until all are dissolved.

| | |
|---|---|
| Compound No. 4 (Table I) | 10% |
| Benzyl alcohol | 30% |
| Calcium dodecylbenzenesulphonate | 5% |
| Nonylphenolethoxylate (13 moles ethylene oxide) | 10% |

| | |
|---|---|
| -continued | |
| Alkyl benzenes | 45% |

EXAMPLE 18

The active ingredient is dissolved in methylene dichloride and the resultant liquid sprayed on to the granules of attapulgite clay. The solvent is then allowed to evaporate to produce a granular composition.

| | |
|---|---|
| Compound No. 4 (Table I) | 5% |
| Attapulgite granules | 95% |

EXAMPLE 19

A composition suitable for use as a seed dressing is prepared by grinding and mixing the three ingredients.

| | |
|---|---|
| Compound No. 57 (Table V) | 50% |
| Mineral oil | 2% |
| China clay | 48% |

EXAMPLE 20

A dustable powder is prepared by grinding and mixing the active ingredient with talc.

| | |
|---|---|
| Compound No. 57 (Table V) | 5% |
| Talc | 95% |

EXAMPLE 21

A suspension concentrate is prepared by ball milling the ingredients to form an aqueous suspension of the ground mixture with water.

| | |
|---|---|
| Compound No. 57 (Table V) | 40% |
| Sodium lignosulphonate | 10% |
| Bentonite clay | 1% |
| Water | 49% |

This formulation can be used as a spray by diluting into water or applied directly to seed.

EXAMPLE 22

A wettable powder formulation is made by mixing together and grinding the ingredients until all are thoroughly mixed.

| | |
|---|---|
| Compound No. 57 (Table V) | 25% |
| Sodium lauryl sulphate | 2% |
| Sodium lignosulphonate | 5% |
| Silica | 25% |
| China clay | 43% |

Other compounds in Tables I to VI can be similarly formulated, as appropriate, depending on their physical characteristics.

EXAMPLE 23

The compounds listed in Table VIII were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous dispersol T or as a solution in acetone or acetone/ethanol which was diluted to the required concentration immediately before use. The formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4=no disease
3=trace-5% of disease on untreated plants
2=6-25% of disease on untreated plants
1=26-59% of disease on untreated plants
0=60-100% of disease on untreated plants
The results are shown in Table VIII.

58 of Table IV, compounds 38 and 57 of Table V and compound 57 of Table VI.

These compounds were tested on a whole plant screen for plant growth species used in this screen are presented in Table IX with the leaf stage at which they were sprayed.

A formulation of each chemical was applied at 4000 ppm (4 kg/ha in a 1000 l/ha field volume) using a track-sprayer and a SS8004E (Teejet) nozzle. Additional tests were done on tomatoes at 2000 and 500 ppm.

After spraying, the plants were grown in a glasshouse with 25° C. day/22° C. night temperatures. The exceptions to this were the temperature cereals wheat and barley, which were grown in 13°-16° C. day/11°-13° C. night temperatures. Supplementary lighting was supplied when necessary to provide an average photoperiod of 16 hours (14 hours minimum).

After 2-6 weeks in the glasshouse, depending on species and time of year, the plants were visually assessed for morphological characteristics against a control plant sprayed with a blank formulation. The results are presented in Table X.

TABLE IX

PLANT MATERIAL USED FOR WHOLE PLANT SCREEN

| Species | Code | Variety | Growth Stage at Treatment | No. Plants per 3" pot | Compost Type* |
|---|---|---|---|---|---|
| Barley | BR | Atem | 1-1.5 leaves | 4 | JIP |
| Wheat | WW | Timmo | 1-1.5 leaves | 4 | JIP |
| Maize | MZ | Earliking | 2½-2¾ leaves | 1 | PEAT |
| Apple | AP | Red Delicious | 4-5 leaves | 1 | JIP |
| Rice | RC | Ishikari | 2-2½ leaves | 4 | JIP |
| Tomato | TO | Ailsa Craig | 2-2½ leaves | 1 | PEAT |

*JIP = John Innes Potting Compost

TABLE VIII

| COMPOUND NO. | TABLE NO. | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLAMOPARA VITICOLA (VINE) | PHYTOPHTHORA INFESTANS (TOMATO) |
|---|---|---|---|---|---|---|---|---|
| 3 | I | 4 | 4 | 4 | 3 | 0 | 3 | — |
| 4 | I | 4 | 4 | 4 | 3 | 0 | 4 | — |
| 7 | I | 4 | 4 | 0 | 2 | 0 | 4 | — |
| 9 | I | 3 | 4 | 4 | 3 | 3 | 4 | 3 |
| 10 | I | 4 | 4 | 4 | 2 | 3 | 4 | 4 |
| 11 | I | 3 | 0 | 4 | 0 | 0 | 4 | 4 |
| 17 | I | 4 | 4 | 4 | 4 | 3 | 4 | 4 |
| 23 | I | 0 | 3 | 4 | 0 | 0 | 0 | 0 |
| 36 | I | 3* | 0* | 0* | 3* | 0* | 0* | — |
| 37 | I | 3 | 0 | 0 | 0 | 0 | 4 | 4 |
| 39 | I | 0 | 2 | 4 | 0 | 0 | 0 | 0 |
| 1 | II | 0 | 3 | 0 | 0 | 0 | 0 | 0 |
| 3 | II | 4 | — | 4 | 2 | — | — | — |
| 4 | II | 4 | 4 | 4 | 4 | 4 | 4 | 3 |
| 9 | II | 4 | 4 | 4 | 4 | 4 | 4 | 4 |
| 17 | II | 4 | 4 | 4 | 3 | 4 | 4 | 3 |
| 24 | II | 4 | 4 | 4 | 1 | 4 | 0 | 0 |
| 36 | II | 3 | 4 | 4 | 3 | 3 | 2 | 0 |
| 39 | II | 0 | 0 | 0 | 0 | 0 | 4 | 0 |
| 40 | II | 4 | 4 | 4 | 3 | 0 | 3 | 0 |
| 17 | III | 4 | 0 | 4 | 2 | 2 | 4 | 3 |
| 58 | IV | 0 | 2 | 0 | 0 | 0 | 0 | — |
| 38 | V | 0 | 0 | 0 | 2 | 0 | 4 | — |
| 57 | V | 4 | 2 | 4 | 0 | 0 | 3 | — |
| 11 | VI | 0 | 0 | 0 | 0 | 0 | 4 | 2 |
| 57 | VI | 0 | 0 | 0 | 0 | 0 | 2 | — |
| 58 | VI | 0 | 0 | 2 | 0 | 0 | 4 | — |
| 60 | VI | 0 | 0 | 0 | 0 | 0 | 1 | 0 |

*25 ppm foliar spray only

EXAMPLE 24

This Example illustrates the plant growth regulating properties of compound 1 of Table I, compounds 3 and

TABLE X

| Compound No. | Table | BR | WW | RC | AP | MZ | TO | TO* | TO+ |
|---|---|---|---|---|---|---|---|---|---|
| 1 | I | | | | | | | | 1 |
| 3 | IV | NT | NT | NT | NT | NT | NT | NT | 1 |
| 58 | IV | | | 1 | | 1 | | NT | NT |
| 38 | V | NT | | NT | NT | 1 | NT | 1A | 2G |
| 57 | V | NT | | NT | NT | | NT | 2G | 2G |
| 57 | VI | NT | | NT | NT | | NT | NT | 1 |

Key:
*2000 ppm
+500 ppm
Retardation 1-3 where 1 = 10-30%
2 = 21-60%
3 = 61-100%
G = Greening effect
A = Apical damage
T = Tillering or side shooting
Blank means less than 10% effect.
NT indicates that the compound was not tested against this species.

We claim:
1. A compound of the formula:

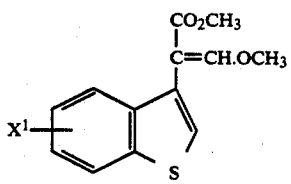

and stereoisomers thereof, wherein $X^1$ is selected from the group consisting of halogen, hydroxy, $C_{1-4}$ alkyl, $C_{1-4}$ alkoxy, halo($C_{1-4}$)alkyl, halo($C_{1-4}$)alkoxy, $C_{1-4}$alkylthio, $C_{1-4}$alkoxy($C_{1-4}$)alkyl, $C_{3-6}$ cycloalkyl, $C_{3-6}$ cycloalkyl($C_{1-4}$)alkyl, aryl, aryloxy, aryl($C_{1-4}$)alkyl, aryl($C_{1-4}$)alkoxy, aryloxy($C_{1-4}$)alkyl, acyloxy, cyano, thiocyanato, nitro, —NR'R", —NHCOR', —NHCONR'R", —CONR'R", —COOR', —OSO$_2$R', —SO$_2$R', —COR', —CR'=NR" or —N=CR'R" in which R' and R" are independently hydrogen, $C_{1-4}$ alkyl, $C_{1-4}$ alkoxy, $c_{1-4}$ alkylthio, $C_{3-6}$ cycloalkyl, $C_{3-6}$ cycloalkyl($C_{1-4}$)alkyl, phenyl or benzyl, the phenyl or benzyl groups being optionally substituted with halogen, $C_{1-4}$ alkyl or $C_{1-4}$ alkoxy; and the aryl moiety of any of aryl, aryloxy, aryl($C_{1-4}$)alkyl, aryl($C_{1-4}$)alkoxy or aryloxy($C_{1-4}$)alkyl referred to above being optionally substituted by one or more substituents selected from the group consisting of halogen, hydroxy, $C_{1-4}$ alkyl, $C_{1-4}$ alkoxy, halo($C_{1-4}$)alkyl, halo($C_{1-4}$)alkoxy, $C_{1-4}$ alkylthio, $C_{1-4}$ alkoxy($C_{1-4}$)alkyl, $C_{3-6}$ cycloalkyl, $C_{3-6}$ cycloalkyl ($C_{1-4}$)alkyl, aryl, aryloxy, aryl($C_{1-4}$)alkyl, aryl($C_{1-4}$)alkoxy, aryloxy($C_{1-4}$)alkyl, acyloxy, cyano, thiocyanato, nitro, —NR'R", —NHCOR', —NHCONR'R", —CONR'R", —COOR', —OSO$_2$R', —SO$_2$R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl in which the phenyl and benzyl groups are optionally substituted with halogen, $C_{1-4}$ alkyl or $C_{1-4}$ alkoxy.

2. A compound according to claim 1 wherein $X^1$ is attached to the 5-position of the 1-benzothiophene ring.

3. A compound according to claim 2 wherein $X^1$ is halogen, hydroxy, $C_{1-4}$ alkyl, $C_{1-4}$ alkoxy, halo($C_{1-4}$)alkyl, halo($C_{1-4}$)alkoxy, phenyl, phenoxy, or -COR' wherein R' is hydrogen, $C_{1-4}$ alkyl, or $C_{1-4}$ alkoxy.

4. The compound of the formula:

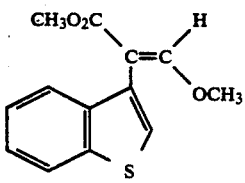

5. The compound of the formula:

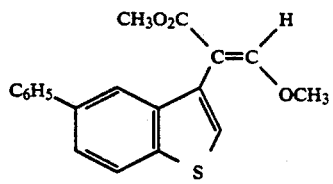

6. A fungicidal composition comprising, as an active ingredient, a fungicidally effective amount of a compound according to claim 1 and a fungicidally acceptable carrier or diluent therefor.

7. A method of combating fungi which comprises applying to plants or seeds, or to their locus, a compound according to claim 1.

8. An insecticidal or plant growth regulating composition comprising, as an active ingredient, an effective amount of a compound according to claim 1 and an acceptable carrier or diluent therefor.

9. A method of killing insect pests which method comprises administering to the insect or to its locus, an effective amount of an insecticidal compound according to claim 1.

10. A method of regulating plant growth which comprises applying to a plant an effective amount of a plant growth regulating compound according to claim 1.

* * * * *